US012629382B2

(12) United States Patent
Bjørsvik et al.

(10) Patent No.: US 12,629,382 B2
(45) Date of Patent: May 19, 2026

(54) THERAPY

(71) Applicant: Vestlandets Innovasjonsselskap AS, Bergen (NO)

(72) Inventors: Hans-René Bjørsvik, Bergen (NO); Per Øyvind Enger, Bergen (NO); Davide Cirillo, Merate (IT); Shahin Sarowar, Nesttun (NO)

(73) Assignee: Vestlandets Innovasjonsselskap AS, Bergen (NO)

( * ) Notice: Subject to any disclaimer, the term of this patent is extended or adjusted under 35 U.S.C. 154(b) by 968 days.

(21) Appl. No.: 17/763,367

(22) PCT Filed: Sep. 25, 2020

(86) PCT No.: PCT/GB2020/052335

§ 371 (c)(1),
(2) Date: Mar. 24, 2022

(87) PCT Pub. No.: WO2021/058979

PCT Pub. Date: Apr. 1, 2021

(65) Prior Publication Data

US 2022/0362265 A1 Nov. 17, 2022

(30) Foreign Application Priority Data

Sep. 25, 2019 (GB) ...................................... 1913785

(51) Int. Cl.

*A61K 31/603* (2006.01)
*A61K 31/196* (2006.01)
*A61K 31/41* (2006.01)
*A61P 35/00* (2006.01)

(52) U.S. Cl.

CPC .......... *A61K 31/603* (2013.01); *A61K 31/196* (2013.01); *A61K 31/41* (2013.01); *A61P 35/00* (2018.01)

(58) Field of Classification Search

CPC .... A61K 31/603; A61K 31/196; A61K 31/41; A61K 41/0038; A61P 35/00

See application file for complete search history.

(56) References Cited

U.S. PATENT DOCUMENTS

| | | | | |
|---|---|---|---|---|
| 8,343,994 B2 * | 1/2013 | Motomura | A61K 31/4523 514/290 |
| 2007/0249647 A1 * | 10/2007 | Vander Jagt | A61K 31/66 514/6.9 |
| 2012/0196874 A1 * | 8/2012 | Watt | C07D 295/073 514/645 |

OTHER PUBLICATIONS

De Filippis, et al.; ChemMedChem, v12, pp. 558-570 (2017). (Year: 2017).*

Patani, G. A. and LaVoie, E. J.; Chemical Reviews, v96, pp. 3147-3176; 1996 (Year: 1196).*

Michelakis, et al.; British Journal of Cancer, v99, pp. 989-994; 2008 (Year: 2008).*

Traversi, et al.; Mutagenesis, v31, pp. 433-441; 2016 (Year: 2016).*

Wrobel, et al.; Journal of Medicinal Chemistry, v32, pp. 2493-2500; 1989 (Year: 1989).*

Patani, G. A. and LaVoie, E. J.; Chemical Reviews, v96, pp. 3147-3176; 1996 (Year: 1996).*

Shukla, et al.; Bioorganic & Medicinal Chemistry Letters, v21, pp. 6184-6187; 2011 (Year: 2011).*

Sleire, et al.; Oncogene, v34, pp. 5951-5959; 2015 (Year: 2015).*

PLoS ONE, vol. 12, No. 1, 2017, Chen et al., "Sensitization of Radioresistant Prostate Cancer Cells by Resveratrol Isolated from Arachis hypogaea Stems".

(Continued)

*Primary Examiner* — Jeffrey S Lundgren
*Assistant Examiner* — W. Justin Youngblood
(74) *Attorney, Agent, or Firm* — Taft Stettinius & Hollister LLP

(57) ABSTRACT

The invention addresses radioresistance in cancer treatment involving radiotherapy and, in particular, limitations associated with the use of the drug sulfasalazine. Specifically, it provides a series of compounds for use as radiosensitizers in the treatment of cancers such as glioblastomas which are lethal and inherently resistant to radiotherapy. In one embodiment, the invention provides compounds of general formula (I), their stereoisomers and pharmaceutically acceptable salts for use as radiosensitizers in the treatment of cancer:

(I)

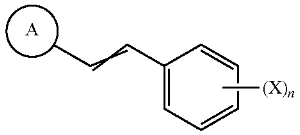

wherein ring A is selected from optionally substituted phenyl, biphenyl and fluorenyl; each X is independently selected from: —$C_{1-6}$ alkyl (preferably $C_{1-3}$ alkyl, e.g. —$CH_3$), —O—$C_{1-6}$ alkyl (preferably —O—$C_{1-3}$ alkyl, e.g. —$OCH_3$), —S—$C_{1-6}$ alkyl (preferably —S—$C_{1-3}$ alkyl, e.g. —$SCH_3$), —OH, —SH, —$CO_2R^1$ (where $R^1$ is H or $C_{1-6}$ alkyl, preferably $C_{1-3}$ alkyl, e.g. —$CH_3$), —$SO_2$—$C_{1-6}$ alkyl (preferably —$SO_2$—$C_{1-3}$ alkyl, e.g. —$SO_2$—$CH_3$), —$SO_2$—$NR^2R^3$ (where $R^2$ is H and $R^3$ is optionally substituted phenyl), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), halogen (e.g. F, Cl or Br), and optionally substituted tetrazolyl; n is an integer from 0 to 5, preferably 0 to 2, e.g. 1 or 2; and  denotes an E or Z double bond.

17 Claims, 1 Drawing Sheet

(56) References Cited

OTHER PUBLICATIONS

International Journal of Biological Sciences, vol. 15, No. 2, 2019, pp. 430-440; Chen et ah, "Polydatin Increases Radiosensitivity by Inducing Apoptosis of Stem Cells in Colorectal Cancer".
Phytomedicine, vol. 23, No. 5, 2016, pp. 566-577, Baek et al., "Resveratrol inhibits STAT3 signaling pathway through the induction of SOCS-1 : Role in apoptosis induction and radiosensitization in head and neck tumor cells".
Cancer Science, vol. 103, No. 6, 2012, pp. 1090-1098; Fang et ah, "Resveratrol enhances radiation sensitivity in prostate cancer by inhibiting cell proliferation and promoting cell senescence and apoptosis".
International Journal of Oncology, vol. 43, No. 6, 2013, pp. 1999-2006; Luo et al., "Resveratrol enhances ionizing radiation-induced premature senescence in lung cancer cells".
Radiation Oncology, vol. 6, 2011, Article No. 144; Rashid et al., "Resveratrol enhances prostate cancer cell response to ionizing radiation. Modulation of the AMPK, Akt and mTOR pathways".
UK Search Report; Intellectual Property Office; United Kingdom Patent Application No. GB1913785.0; Mar. 19, 2020; 5 pages.
Intemational Search Report; International Searching Authority; International Patent Application No. PCT/GB2020/052335; Jan. 12, 2021; 5 pages.
Written Opinion; International Searching Authority; International Patent Application No. PCT/GB2020/052335; Jan. 12, 2021; 9 pages.
International Preliminary Report on Patentability; International Searching Authority; International Patent Application No. PCT/GB2020/052335; Apr. 7, 2022; 7 pages.
Shukla et al., "Inhibition of Xc- transporter-mediated cystine update by sulfasalazine analogs", Bioorganic & Medicinal Chemistry Letters, vol. 21, 2011, pp. 6184-6187.

* cited by examiner

A)
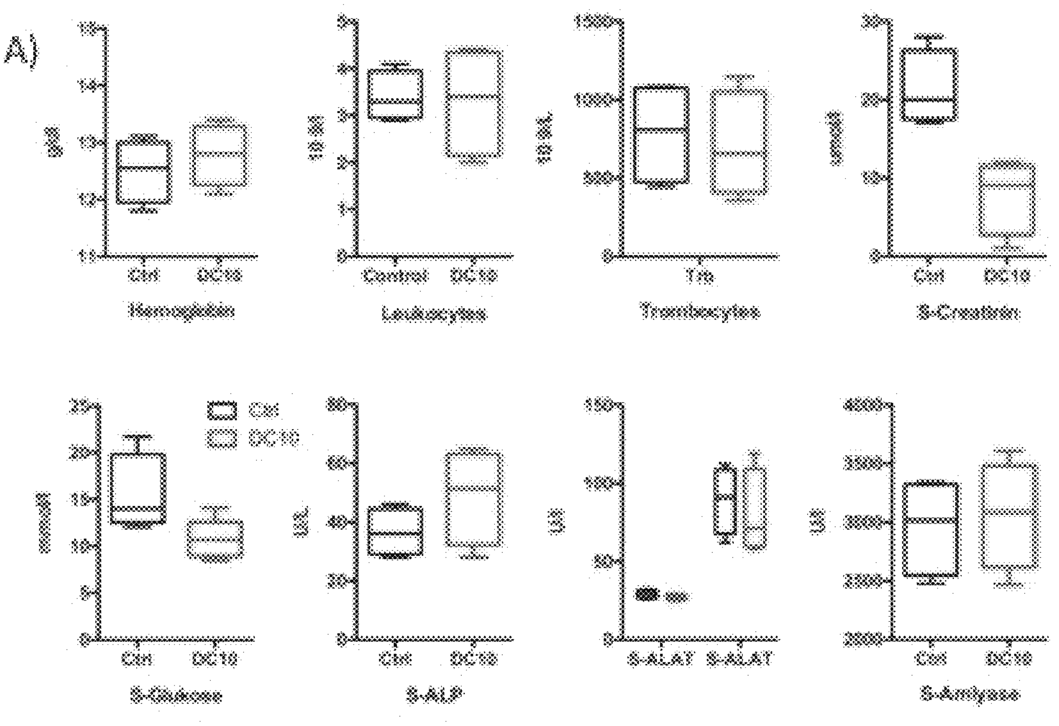
B)
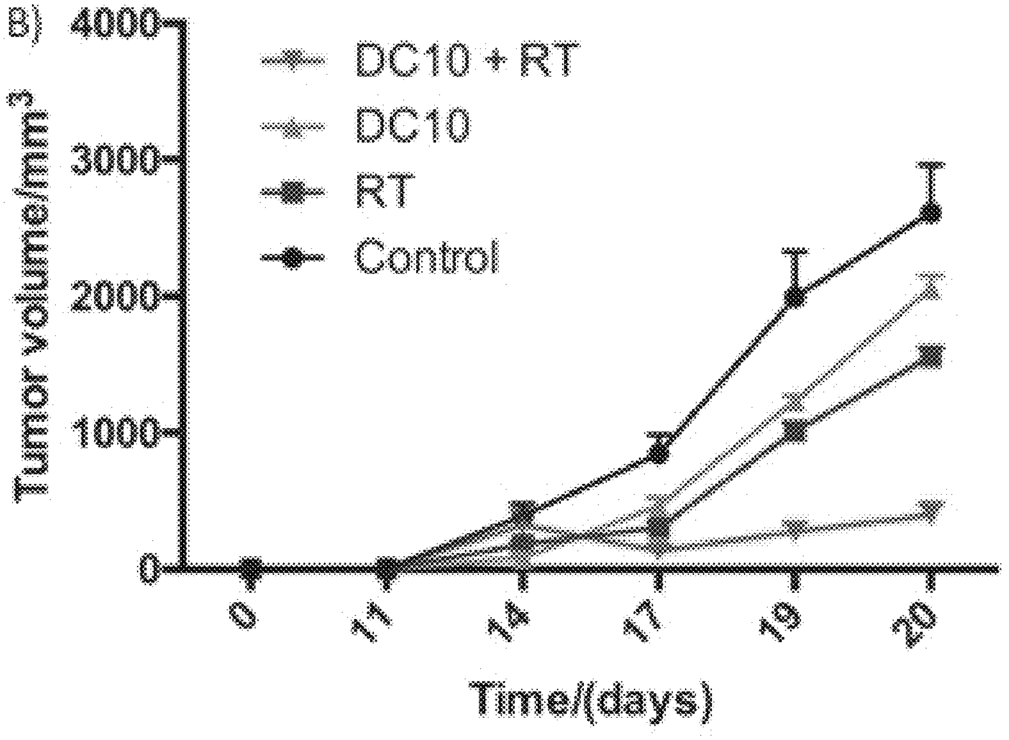

THERAPY

CROSS-REFERENCE TO RELATED APPLICATIONS

This application is a U.S. National Phase of International PCT Application No. PCT/GB2020/052335, which was filed on Sep. 25, 2020, and which claims priority to United Kingdom Patent Application No. 1913785.0, which was filed on Sep. 25, 2019. Those applications are incorporated by reference herein in their entireties.

TECHNICAL FIELD

The present invention relates to the field of cancer treatment.

More specifically, the invention relates to the use of certain compounds as radiosensitizers in combination with radiation treatment of cancers. Such combination therapy is particularly suitable for the treatment of cancers such as glioblastomas which are lethal cancers and inherently resistant to radiotherapy.

The invention further relates to certain novel compounds, pharmaceutical compositions containing them, and their use in such treatment methods.

BACKGROUND

The global burden of cancer is increasing, and it ranks as the first or second cause of premature deaths in almost 100 countries. The treatment of tumours with ionizing radiation, generally known as "radiation therapy" or "radiotherapy", is extensively used in cancer therapy. It results in the destruction of tumour cells as well as the inhibition of tumour cell growth, either by a direct effect on DNA, or indirectly via intermediate radiation products such as free radicals. DNA damage subsequently leads to apoptosis when the cells pass through check points during the cell cycle.

Radiotherapy is a mainstay treatment for many cancers and their associated metastatic disease, however, the most common cancer types such as melanoma, breast, prostate, lung and colon cancer, as well as glioblastoma multiforme (GBM), exhibit varying degrees of radio-resistance. Studies have shown, for example, that cancer cells synthesize antioxidants at increased rates to scavenge free radicals that are produced following radiotherapy. Due to their radio-resistance many cancers remain incurable in the metastatic stage and account for a large proportion of cancer-related deaths. Since the incidence of radio-resistant malignancies will increase, according to WHO estimates, strategies to potentiate radiotherapy are urgently needed.

Sulfasalazine (herein also referred to as "SAS") has been approved for medical use and is primarily used as a medication in the treatment of inflammatory bowel diseases and rheumatoid arthritis:

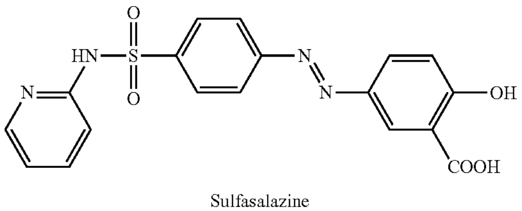 [SMILES: O=C(O)c1cc(/N=N/c2ccc(S(=O)(=O)Nc3ccccn3)cc2)ccc1O]

Sulfasalazine

It has also been reported that SAS acts as a radiosensitizer by blocking the cell membrane xCT antiport and its uptake of cysteine, which is the rate-limiting step in the biosynthesis of glutathione (GSH), one of the most important antioxidants in mammalian cells. All cells, including cancer cells, rely upon GSH as a major defence system against oxidative stress; cells depleted of GSH lack protection from free radicals induced by radiotherapy. Notably the xCT antiport is expressed at elevated levels in many cancers. For instance, it is highly expressed in GBMs but barely detectable in normal brain, providing a therapeutic window for targeting xCT. SAS has, for example, been shown to act as a radiosensitizer on various glioma cells in vitro and in human GMBs xenografted into nude rats. It effectively blocks GSH synthesis leading to cell death as well as potentiating the effect of gamma knife radiosurgery (GKR) (see, for example, Cancer and Metastasis Reviews 33: 469-96, 2014 and Oncogene 34: 5951-5959, 2015).

However, SAS has various side effects when used in combination with chemotherapy which are attributed to the molecular moiety sulfapyridine. SAS was originally designed as a prodrug in which the diazo bond (Ar—N═N—Ar) is cleaved by bacteria (diazoreductases) in the intestines producing 5-amino-2-hydroxybenzoic acid (mesalazine or 5-ASA) and 4-amino-N-(pyridin-2-yl)benzenesulfonamide (sulfapyridine), both without xCT activity, thereby limiting its systemic uptake and clinical potential (Cancer Cell 24: 450-65, 2013).

A need thus exists for alternative strategies to overcome radioresistance in cancer treatment using radiotherapy and, in particular, to address limitations associated with the use of the drug sulfasalazine.

The inventors now propose a series of compounds for use as radiosensitizers to be administered in conjunction with radiotherapy. Such compounds have been modeled in GBM and it has been shown that these can increase GSH levels. Such effects are expected to extend to other types of radioresistant cancers, including but not limited to breast and lung cancer.

Many of the compounds described herein and which are proposed for use as radiosensitizers are novel and the invention also extends to the compounds themselves, as well as to pharmaceutical compositions which contain them and their medical use generally.

SUMMARY

The compounds proposed for use in the invention each comprise a core structure which effectively blocks rotation in some segments of the molecular scaffold. Although not wishing to be bound by theory, this core structure is considered to be key to their activity (and thus to operate as the pharmacophore). Rotation may be blocked, for example, by a core structure based on styrene. Bioisosteres of this core structure also find use in the invention and thus the invention further extends to the use of compounds having an alkynyl, naphthenyl or para-terphenyl core.

In one aspect the invention provides a compound of general formula (I), a stereoisomer, or a pharmaceutically acceptable salt thereof, for use as a radiosensitizer in the treatment of cancer:

(I)

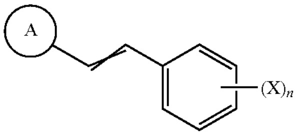

wherein:

ring A is selected from optionally substituted phenyl, biphenyl and fluorenyl;

each X is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$SO_2$—$C_{1-6}$ alkyl (preferably —$SO_2$—$C_{1-3}$ alkyl, e.g. —$SO_2$—$CH_3$), —$SO_2$—$NR^2R^3$ (where $R^2$ is H and $R^3$ is optionally substituted phenyl), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), halogen (e.g. F, Cl or Br), and optionally substituted tetrazolyl;

n is an integer from 0 to 5, preferably 0 to 2, e.g. 1 or 2; and

 denotes an E or Z double bond.

In another aspect the invention provides a compound of general formula (II), a stereoisomer, or a pharmaceutically acceptable salt thereof, for use as a radiosensitizer in the treatment of cancer:

(II)

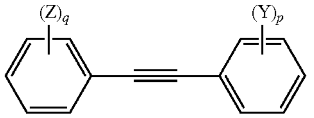

wherein:

each Y is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

each Z is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e,g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e,g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

p is an integer from 0 to 5, preferably 0 to 2, e.g. 2; and q is an integer from 0 to 5, preferably 0 to 2, e.g. 0.

In another aspect the invention provides a compound of general formula (III), a stereoisomer, or a pharmaceutically acceptable salt thereof, for use as a radiosensitizer in the treatment of cancer:

(III)

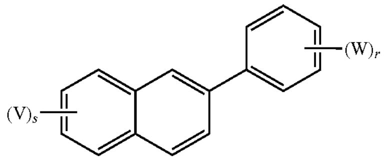

wherein:

each W is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

each V is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

r is an integer from 0 to 5, preferably 2 to 4, e.g. 2 or 4; and s is an integer from 0 to 5, preferably 0.

In another aspect the invention provides a compound of general formula (IV), a stereoisomer, or a pharmaceutically acceptable salt thereof, for use as a radiosensitizer in the treatment of cancer:

(IV)

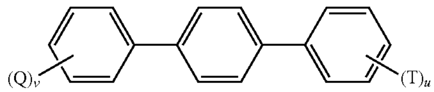

wherein:

each T is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

each Q is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

u is an integer from 0 to 5, preferably 2 to 4, e.g. 2; and v is an integer from 0 to 5, preferably 0.

In another aspect the invention provides a compound of general formula (I), (II), (III) or (IV), or a stereoisomer, or pharmaceutically acceptable salt thereof, for use in therapy.

In another aspect the invention provides a pharmaceutical composition comprising a compound of general formula (I), (II), (III) or (IV), or a stereoisomer, or pharmaceutically acceptable salt thereof, together with one or more pharmaceutically acceptable carriers, excipients or diluents.

In a further aspect the invention provides the use of any of the compounds of general formula (I), (II), (III) or (IV), or a stereoisomer, or pharmaceutically acceptable salt thereof, in the manufacture of a medicament for use as a radiosensitizer in the treatment of cancer.

In another aspect the invention provides a method of treating cancer, said method comprising the step of administering to a patient in need thereof (e.g. a human subject) a pharmaceutically effective amount of a compound of general formula (I), (II), (III) or (IV), or a stereoisomer, or pharmaceutically acceptable salt thereof, in combination with radiotherapy.

In a yet further aspect, the invention provides certain novel compounds of general formula (I), (II), (III) and (IV) as herein described, their stereoisomers, and pharmaceutically acceptable salts. Processes for the preparation of such compounds also form a further aspect of the invention.

DETAILED DESCRIPTION

Definitions

As used herein, the term "alkyl" refers to a saturated hydrocarbon group and is intended to cover both straight-chained and branched alkyl groups. Examples of such groups include methyl, ethyl, n-propyl, iso-propyl, n-butyl, tert-butyl, sec-butyl, n-pentyl, iso-pentyl, neo-pentyl, n-hexyl, 2-methylbutyl, 2-methylpentyl, 2-ethylbutyl, 3-methylpentyl, and 4-methylpentyl. An alkyl group preferably contains from 1-6 carbon atoms, more preferably 1-4 carbon atoms, e.g. 1-3 carbon atoms. Unless otherwise specified, any alkyl group may be substituted in one or more positions with a suitable substituent. Where more than one substituent group is present, these may be the same or different. Suitable substituents include —OH, —$OC_{1-3}$ alkyl (e.g. —$OCH_3$), —$NH_2$, —CN, and —$NO_2$ groups, or halogen atoms (e.g. F, Cl or Br).

The term "halogen" or "halogen atom" as used herein refers to —F, —Cl, —Br or —I.

Unless otherwise stated, all substituents are independent of one another.

In the case where a subscript is the integer 0 (i.e. zero), it is intended that the group to which the subscript refers is absent.

The compounds herein described may contain one or more stereocenters and may therefore exist in different stereoisomeric forms. The term "stereoisomer" refers to compounds which have identical chemical constitution, but which differ in respect of the spatial arrangement of the atoms or groups. Examples of stereoisomers are enantiomers and diastereomers. The term "enantiomers" refers to two stereoisomers of a compound which are non-superimposable mirror images of one another. The term "diastereoisomers" refers to stereoisomers with two or more stereocenters which are not mirror images of one another. The invention is considered to extend to diastereomers and enantiomers, as well as racemic mixtures and enantioenriched mixtures in which the ratio of enantiomers is other than 1:1.

The compounds herein described may be resolved into their enantiomers and/or diastereomers. For example, where these contain only one chiral center, these may be provided in the form of a racemate or racemic mixture (a 50:50 mixture of enantiomers) or may be provided as pure enantiomers, i.e. in the R- or S-form. Any of the compounds which occur as racemates may be separated into their enantiomers by methods known in the art, such as column separation on chiral phases or by recrystallization from an optically active solvent. Those compounds with at least two asymmetric carbon atoms may be resolved into their diastereomers on the basis of their physical-chemical differences using methods known per se, e.g. by chromatography and/or fractional crystallization, and where these compounds are obtained in racemic form, they may subsequently be resolved into their enantiomers.

Where any of the compounds herein described include a carbon-carbon double bond this may be present in the E-configuration or the Z-configuration. Certain compounds herein described may therefore exist as E- or Z-isomers. The invention extends to the use of both E- and Z-isomers of any of the compounds herein described, and to mixtures of these isomers.

The term “pharmaceutically acceptable salt” as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilizes the charge on the parent compound. If the compound of the invention is a base, a suitable pharmaceutically acceptable salt may be prepared by reaction of the free base with an organic or inorganic acid. If the compound of the invention is an acid, a suitable pharmaceutically acceptable salt may be prepared by reaction of the free acid with an organic or inorganic base. Non-limiting examples of suitable salts are described herein.

The term “pharmaceutically acceptable” means that the compound or composition is chemically and/or toxicologically compatible with other components of the formulation or with the patient (e.g. human) to be treated.

By “a pharmaceutical composition” is meant a composition in any form suitable to be used for a medical purpose.

As used herein, the term “cancer” refers to cells undergoing abnormal proliferation. Growth of such cells typically causes the formation of a tumour. Cancerous cells may be benign, pre-malignant or malignant. Such cells may be invasive and/or have the ability to metastasize to other locations in the body. The term cancer, as used herein, includes cancerous growths, tumours, and their metastases. The term “tumour”, as used herein, refers to an abnormal mass of tissue containing cancerous cells.

As used herein, the term “metastasis” refers to the spread of malignant tumour cells from one organ or part of the body to another non-adjacent organ or part of the body. Cancer cells may break away from a primary tumour, enter the lymphatic and blood systems and circulate to other parts of the body (e.g. to normal tissues). Here they may settle and grow within the normal tissues. When tumour cells metastasize, the new tumours may be referred to as a “secondary” or metastatic cancer or tumour.

The terms “radiotherapy” and “radiation therapy” are used interchangeably herein to refer to the treatment of cancer with ionizing radiation. Ionizing radiation deposits energy that injures or destroys cells in the target tissue by damaging their genetic material, making it impossible for these cells to continue to grow. The term “ionizing radiation” is conventionally used in the field of cancer treatment and includes any high-energy radiation which is used to kill or damage cancer cells and/or to shrink tumours, such as X-rays, gamma rays, neutrons, or protons.

The terms “treating cancer” and “treatment of cancer” are used interchangeably herein and refer to any method that produces one or more anti-cancer effects in a human or non-human animal (e.g. a non-human mammal). Such effects include, but are not limited to, anti-tumour effects, response rate, time to disease progression and overall survival rate. Anti-tumour effects include, but are not limited to, inhibition of tumour growth, tumour growth delay, tumour regression, shrinkage of a tumour, increased time to regrowth of a tumour on cessation of treatment, and slowing of disease progression. Both human and veterinary treatments are within the scope of the present invention, although primarily the invention is aimed at the treatment of humans.

As used herein, a “pharmaceutically effective amount” relates to an amount of a compound that, when administered to a subject for the treatment of cancer, will lead to the desired therapeutic effect. The effective amount will vary depending on the cancer to be treated, the compound to be administered, the severity of the cancer, the age and relative health of the subject, the route and form of administration, whether the treatment is monotherapy or combination therapy, the judgement of the clinician, and other factors. As will be understood, the effective amount of the compound for use according to the invention may also be dependent on the choice of radiation therapy. While individual patient needs may vary, determination of optimal ranges for effective amounts of the compound is within the capability of those skilled in the art.

The inventors have found that the compounds herein described can potentiate xCT inhibition thus depleting glutathione levels in cells. The ability of the compounds to deplete GSH levels is demonstrated herein in glioma, melanoma and breast cancer cell lines. These findings lead to the proposed use of the compounds as radiosensitizers in cancer therapy in subjects, e.g. humans, to improve or increase the response of tumours to radiotherapy treatment.

In one aspect the invention provides a compound of general formula (I), a stereoisomer, or a pharmaceutically acceptable salt thereof, for use as a radiosensitizer in the treatment of cancer:

(I)

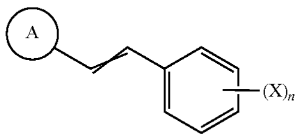

wherein:

ring A is selected from optionally substituted phenyl, biphenyl and fluorenyl;

each X is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$SO_2$—$C_{1-6}$ alkyl (preferably —$SO_2$—$C_{1-3}$ alkyl, e.g. —$SO_2$—$CH_3$), —$SO_2$—$NR^2R^3$ (where $R^2$ is H and $R^3$ is optionally substituted phenyl), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), halogen (e.g. F, Cl or Br), and optionally substituted tetrazolyl;

n is an integer from 0 to 5, preferably 0 to 2, e.g. 1 or 2; and

 denotes an E or Z double bond.

The carbon-carbon double bond in the compounds of formula (I) may be present in the E or Z configuration, but preferably it is an E double bond. In one embodiment, the compounds for use in the invention may thus be of general formula (Ia), or a pharmaceutically acceptable salt thereof:

(Ia)

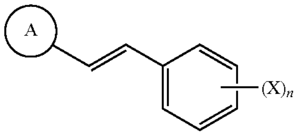

wherein A, X and n are as herein defined.

In one embodiment of formula (I) or (Ia), ring A is unsubstituted.

In another embodiment, ring A in formula (I) or formula (Ia) is substituted by one or more (e.g. 1 or 2) substituent groups independently selected from any of the following:

—$C_{1-6}$ alkyl (preferably $C_{1-3}$ alkyl, e.g. —$CH_3$),
—O—$C_{1-6}$ alkyl (preferably —O—$C_{1-3}$ alkyl, e.g. —$OCH_3$),
—S—$C_{1-6}$ alkyl (preferably —S—$C_{1-3}$ alkyl, e.g. —$SCH_3$),
—OH,
—SH,
—$CO_2R^1$ (where $R^1$ is H or $C_{1-6}$ alkyl, preferably $C_{1-3}$ alkyl, e.g. —$CH_3$),
—$SO_2$—$C_{1-6}$ alkyl (preferably —$SO_2$—$C_{1-3}$ alkyl, e.g. —$SO_2$—$CH_3$),
—$SO_2$—$NR^2R^3$ (where $R^2$ is H and $R^3$ is optionally substituted phenyl),
—$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and
halogen (e.g. F, Cl or Br).

In some embodiments, the substituents present on ring A may be selected from the following:

—$C_{1-6}$ alkyl (preferably $C_{1-3}$ alkyl, e.g. —$CH_3$),
—O—$C_{1-6}$ alkyl (preferably —O—$C_{1-3}$ alkyl, e.g. —$OCH_3$),
—S—$C_{1-6}$ alkyl (preferably —S—$C_{1-3}$ alkyl, e.g. —$SCH_3$),
—$SO_2$—$C_{1-6}$ alkyl (preferably —$SO_2$—$C_{1-3}$ alkyl, e.g. —$SO_2$—$CH_3$),
—$SO_2$—$NR^2R^3$ (where $R^2$ is H and $R^3$ is optionally substituted phenyl), and
halogen (e.g. F, Cl or Br).

In one embodiment of formula (I) and formula (Ia), ring A is phenyl. It may be unsubstituted phenyl. Alternatively, ring A may be a phenyl group substituted by 1 or 2 substituent groups (e.g. 1 group) independently selected from halogen (e.g. —F), —S—$CH_3$, —$SO_2$—$CH_3$, and —$SO_2$—NHPh (where Ph=phenyl).

In another embodiment of formula (I) and formula (Ia), ring A is biphenyl. Where ring A is biphenyl, in certain embodiments it will be unsubstituted. The biphenyl group may be linked to the remainder of the molecule in any suitable position. For example, ring A may be selected from any of the following (where * denotes the point of attachment to the remainder of the molecule):

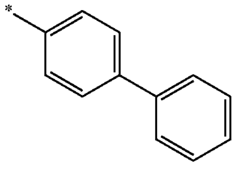

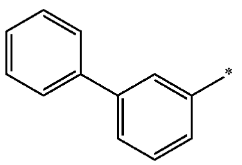

-continued

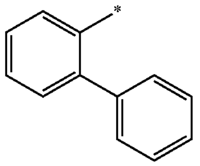

In another embodiment of formula (I) and formula (Ia), ring A is fluorenyl. The fluorenyl group may be linked to the remainder of the molecule at any position but typically it will be linked via one of its benzene rings.

Where ring A is fluorenyl, it may be unsubstituted. In some embodiments, however, it will be substituted by 1 or 2 (e.g. by 2) alkyl groups (e.g. —$CH_3$ groups). In one embodiment of formula (I) and (Ia), ring A is 9,9-dimethyl-9H-fluorenyl.

In formula (I) and (Ia), n is preferably 1 or 2. Preferred substituent groups X include —$OCH_3$, —$CO_2H$, —OH, —$NH_2$, tetrazolyl, and —NH—$COCH_3$. In some embodiments, at least one group X is —$CO_2H$. Preferably, each X is independently —$OCH_3$, —$CO_2H$, or —OH. In certain embodiments, 2 substituent groups X may be present on the phenyl ring and are selected from the following combinations: —$OCH_3$ and —$CO_2H$; and —$CO_2H$ and —OH.

In another aspect the invention provides a compound of general formula (II), a stereoisomer, or a pharmaceutically acceptable salt thereof, for use as a radiosensitizer in the treatment of cancer:

(II)

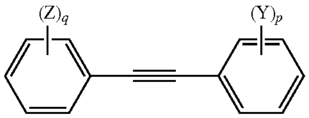

wherein:

each Y is independently selected from:

—$C_{1-6}$ alkyl (preferably $C_{1-3}$ alkyl, e.g. —$CH_3$),
—O—$C_{1-6}$ alkyl (preferably —O—$C_{1-3}$ alkyl, e.g. —$OCH_3$),
—S—$C_{1-6}$ alkyl (preferably —S—$C_{1-3}$ alkyl, e.g. —$SCH_3$),
—OH,
—SH,
—$CO_2R^1$ (where $R^1$ is H or $C_{1-6}$ alkyl, preferably $C_{1-3}$ alkyl, e.g. —$CH_3$),
—$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and
halogen (e.g. F, Cl or Br);

each Z is independently selected from:

—$C_{1-6}$ alkyl (preferably $C_{1-3}$ alkyl, e.g. —$CH_3$),
—O—$C_{1-6}$ alkyl (preferably —O—$C_{1-3}$ alkyl, e.g. —$OCH_3$),
—S—$C_{1-6}$ alkyl (preferably —S—$C_{1-3}$ alkyl, e.g. —$SCH_3$),
—OH,
—SH,
—$CO_2R^1$ (where $R^1$ is H or $C_{1-6}$ alkyl, preferably $C_{1-3}$ alkyl, e.g. —$CH_3$),
—$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

p is an integer from 0 to 5, preferably 0 to 2, e.g. 2; and q is an integer from 0 to 5, preferably 0 to 2, e.g. 0.

In formula (II), q is preferably 0.

In formula (II), p is preferably 2. In certain embodiments, Y is selected from —$OCH_3$ and —$CO_2H$.

In another aspect the invention provides a compound of general formula (III), a stereoisomer, or a pharmaceutically acceptable salt thereof, for use as a radiosensitizer in the treatment of cancer:

(III)

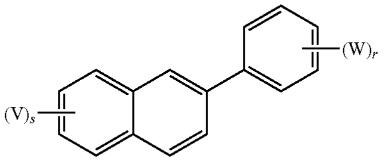

wherein:

each W is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

each V is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

r is an integer from 0 to 5, preferably 2 to 4, e.g. 2 or 4; and s is an integer from 0 to 5, preferably 0.

In formula (III), s is preferably 0.

In formula (III), r is preferably 2 or 4.

In certain embodiments of formula (III), each W is independently selected from:

—O—$C_{1-6}$ alkyl (preferably —O—$C_{1-3}$ alkyl, e.g. —$OCH_3$),

—$CO_2R^1$ (where $R^1$ is H or $C_{1-6}$ alkyl, preferably $C_{1-3}$ alkyl, e.g. —$CH_3$), and

—OH.

In another aspect the invention provides a compound of general formula (IV), a stereoisomer, or a pharmaceutically acceptable salt thereof, for use as a radiosensitizer in the treatment of cancer:

(IV)

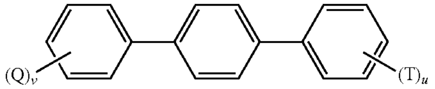

wherein:

each T is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$), —$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

each Q is independently selected from:

—$C_{1-6}$ alkyl (preferably $C_{1-3}$ alkyl, e.g. —$CH_3$),

—O—$C_{1-6}$ alkyl (preferably —O—$C_{1-3}$ alkyl, e.g. —$OCH_3$),

—S—$C_{1-6}$ alkyl (preferably —S—$C_{1-3}$ alkyl, e.g. —$SCH_3$),

—OH,

—SH,

—$CO_2R^1$ (where $R^1$ is H or $C_{1-6}$ alkyl, preferably $C_{1-3}$ alkyl, e.g. —$CH_3$)

—$NR^4R^5$ (wherein $R^4$ and $R^5$ are independently selected from H, $C_{1-6}$ alkyl (preferably $C_{1-3}$ alkyl, e.g. —$CH_3$), and —CO—$C_{1-6}$ alkyl (preferably —CO—$C_{1-3}$ alkyl, e.g. —CO—$CH_3$), and halogen (e.g. F, Cl or Br);

u is an integer from 0 to 5, preferably 2 to 4, e.g. 2; and v is an integer from 0 to 5, preferably 0.

In formula (IV), v is preferably 0.

In formula (IV), u is preferably 2.

In certain embodiments of formula (IV), each T is independently selected from:

—$CO_2R^1$ (where $R^1$ is H or $C_{1-6}$ alkyl, preferably $C_{1-3}$ alkyl, e.g. —$CH_3$), and

—OH.

Examples of compounds for use in accordance with the invention include, but are not limited to the following and their stereoisomers, and pharmaceutically acceptable salts:

| Compound No. | IUPAC compound name and CAS No. (where appropriate) | Structure |
|---|---|---|
| DC01 | (E)-2-methoxy-5-styrylbenzoic acid | 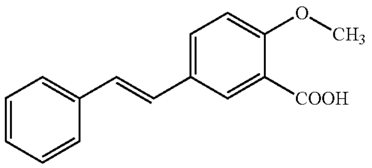 [SMILES: COc1ccc(/C=C/c2ccccc2)cc1C(=O)O] |
| DC02 | (E)-2-hydroxy-5-styrylbenzoic acid CAS No. 1072937-49-5 | 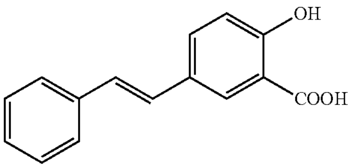 [SMILES: O=C(O)c1cc(/C=C/c2ccccc2)ccc1O] |
| DC03 | (Z)-2-methoxy-5-styrylbenzoic acid | 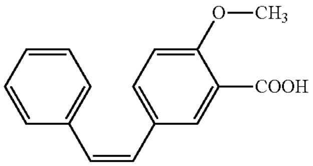 [SMILES: COc1ccc(/C=C\c2ccccc2)cc1C(=O)O] |
| DC04 | 2-methoxy-5-(phenylethynyl) benzoic acid | 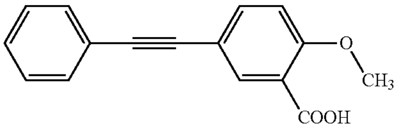 [SMILES: COc1ccc(C#Cc2ccccc2)cc1C(=O)O] |
| DC05 | 2-methoxy-5-(naphthalen-2-yl)benzoic acid | 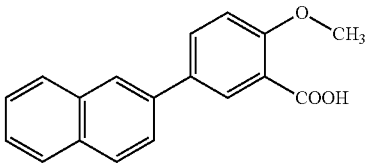 [SMILES: COc1ccc(-c2ccc3ccccc3c2)cc1C(=O)O] |
| DC07 | (E)-5-(4-fluorostyryl)-2-hydroxybenzoic acid | 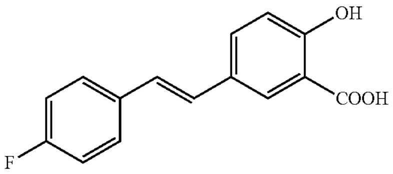 [SMILES: O=C(O)c1cc(/C=C/c2ccc(F)cc2)ccc1O] |
| DC08 | (E)-2-hydroxy-5-(4-(methylthio) styryl)benzoic acid | 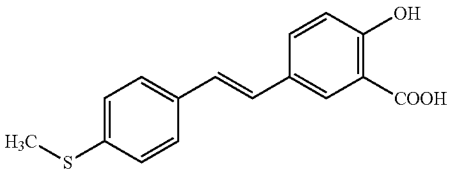 [SMILES: CSc1ccc(/C=C/c2ccc(O)c(C(=O)O)c2)cc1] |
| DC10 | (E)-5-(2-([1,1'-biphenyl]-4-yl)vinyl)-2-hydroxybenzoic acid | 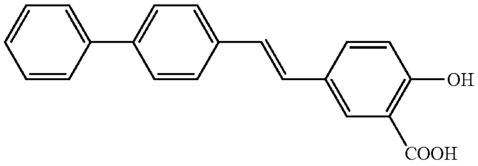 [SMILES: O=C(O)c1cc(/C=C/c2ccc(-c3ccccc3)cc2)ccc1O] |
| DC11 | 2-hydroxy-5-(naphthalen-2-yl)benzoic acid CAS No. 151826-05-0 | 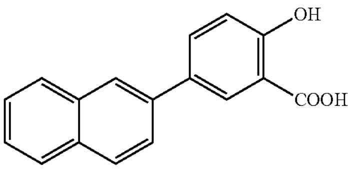 [SMILES: O=C(O)c1cc(-c2ccc3ccccc3c2)ccc1O] |

-continued

| Compound No. | IUPAC compound name and CAS No. (where appropriate) | Structure |
|---|---|---|
| DC12 | (E)-2-amino-5-styrylbenzoic acid | 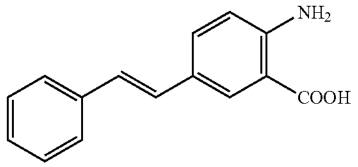 [SMILES: Nc1ccc(/C=C/c2ccccc2)cc1C(=O)O] |
| DC13 | (E)-2-hydroxy-5-(4-(methylsulfonyl) styryl)benzoic acid | 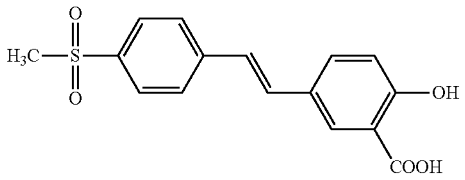 [SMILES: CS(=O)(=O)c1ccc(/C=C/c2ccc(O)c(C(=O)O)c2)cc1] |
| DC14 | (E)-2-hydroxy-5-(4-(N-phenylsulfamoyl)styryl) benzoic acid | 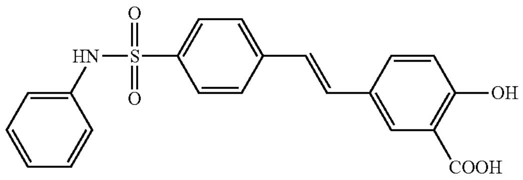 [SMILES: O=C(O)c1cc(/C=C/c2ccc(S(=O)(=O)Nc3ccccc3)cc2)ccc1O] |
| DC15 | (E)-4-styryl-2-(1H-tetrazol-5-yl)phenol | 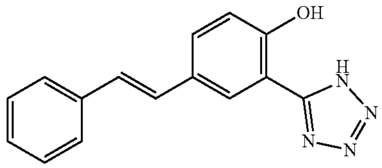 [SMILES: Oc1ccc(/C=C/c2ccccc2)cc1-c1nnn[nH]1] |
| DC16 | (E)-2-acetamido-5-styrylbenzoic acid CAS No. 380365-20-8 | 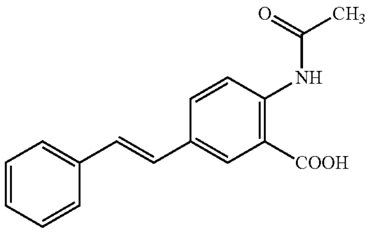 [SMILES: CC(=O)Nc1ccc(/C=C/c2ccccc2)cc1C(=O)O] |
| DC17 | 4-hydroxy-[1,1':4',1"-terphenyl]-3-carboxylic acid CAS No. 1639462-44-4 | 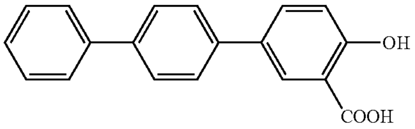 [SMILES: O=C(O)c1cc(-c2ccc(-c3ccccc3)cc2)ccc1O] |
| DC18 | (E)-5-(2-([1,1'-biphenyl]-3-yl)vinyl)-2-hydroxybenzoic acid | 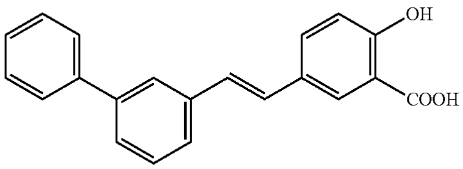 [SMILES: O=C(O)c1cc(/C=C/c2cccc(-c3ccccc3)c2)ccc1O] |
| DC19 | (E)-5-(2-([1,1'-biphenyl]-2-yl)vinyl)-2-hydroxybenzoic acid | 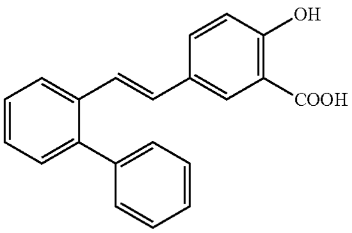 [SMILES: O=C(O)c1cc(/C=C/c2ccccc2-c2ccccc2)ccc1O] |

-continued

| Compound No. | IUPAC compound name and CAS No. (where appropriate) | Structure |
|---|---|---|
| DC20 | 6-hydroxy-2,4-dimethyl-3-(naphthalen-2-yl) benzoic acid | 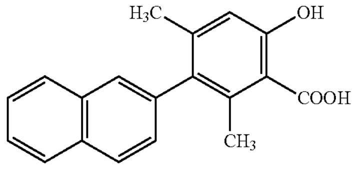 [SMILES: Cc1cc(O)c(C(=O)O)c(C)c1-c1ccc2ccccc2c1] |
| DC21 | (E)-5-(2-(9,9-dimethyl-9H-fluoren-2-yl)vinyl)-2-hydroxybenzoic acid | 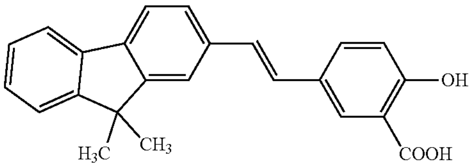 [SMILES: CC1(C)c2ccccc2-c2ccc(/C=C/c3ccc(O)c(C(=O)O)c3)cc21] |

Certain compounds described herein are novel and these form a further aspect of the invention. Thus, in a further aspect the invention provides compounds of general formula (I), (II), (III) and (IV) as herein described, their stereoisomers and pharmaceutically acceptable salts, other than the following compounds:

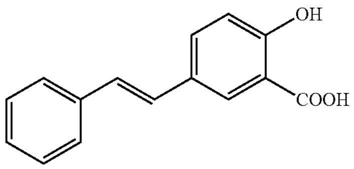

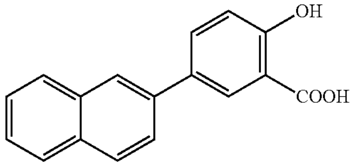

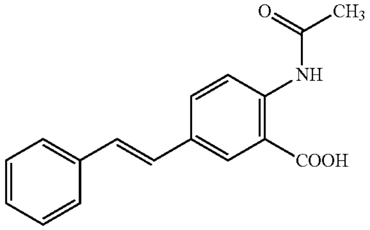

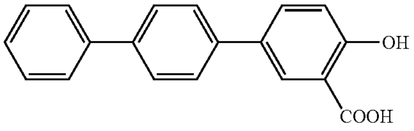

Novel compounds according to the invention include, in particular, compound Nos. DC01, DC03, DC04, DC05, DC07, DC08, DC10, DC12, DC13, DC14, DC15, DC18, DC19, DC20 and DC21 listed herein, as well as their stereoisomers and pharmaceutically acceptable salts thereof.

Any of the novel compounds of formulae (I), (II), (III) and (IV) according to the invention may further be provided in the form of a pharmaceutically acceptable salt.

Any of the compounds herein described may be converted into a pharmaceutically acceptable salt with an inorganic or organic acid or base.

A suitable pharmaceutically acceptable salt of a compound herein described is, for example, an acid addition salt of a compound which is sufficiently basic, for example, an acid addition salt with, for example, an inorganic or organic acid. Acids which may be used for this purpose include hydrochloric acid, hydrobromic acid, nitric acid, sulphuric acid, sulphonic acid, methanesulphonic acid, phosphoric acid, fumaric acid, succinic acid, lactic acid, citric acid, tartaric acid, malic acid, malonic acid, maleic acid, acetic acid, trifluoroacetic acid and ascorbic acid, para-toluene sulphonic acid, 2-mesitylene sulphonic acid, 1,2-ethanedisulphonic, adipic, aspartic, benzenesulphonic, benzoic, ethanesulphonic or nicotinic acid.

In addition a suitable pharmaceutically acceptable salt of a compound herein described, is, for example, a base addition salt of a compound which is sufficiently acidic, for example, a metal salt, for example, a sodium, potassium, calcium, magnesium, zinc or aluminium salt, an ammonium salt, or a salt with an organic base which affords a physiologically acceptable cation, which includes quaternary ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl) amine, hydroxyethyl diethylamine, (IR,2S)-2-hydroxyinden-I-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine, and organic amines such as diethylamine, triethylamine, ethanolamine, diethanolamine, cyclohexylamine and dicyclohexylamine.

Procedures for salt formation are conventional in the art.

As will be understood, the compounds described herein may exist in various stereoisomeric forms, including enantiomers, diastereomers, and mixtures thereof. The invention encompasses all optical isomers of the compounds described herein and mixtures of optical isomers. Hence, compounds that exist as diastereomers, racemates and/or enantiomers are within the scope of the invention.

The compounds of formula (I), (II), (III) and (IV) are either known in the art, or can be prepared by methods known to those skilled in the art. Any of the compounds herein described which are not known in the art may be prepared from readily available starting materials using synthetic methods known in the art such as those described in known textbooks, for example, in Advanced Organic Chemistry (March, Wiley Interscience, 5th Ed. 2001) or Advanced Organic Chemistry (Carey and Sundberg, KA/PP, 4th Ed. 2001).

The following schemes show general methods for preparing the compounds herein described. Such methods form a further aspect of the invention. The compounds used as starting materials are either known from the literature or may be commercially available. Alternatively, these may readily be obtained by methods known from the literature. As will be understood, other synthetic routes may be used to prepare the compounds using different starting materials, different reagents and/or different reaction conditions. A more detailed description of how to prepare the compounds in accordance with the invention is found in the Examples.

Scheme 1: General scheme for the synthesis of compounds of formula (I)

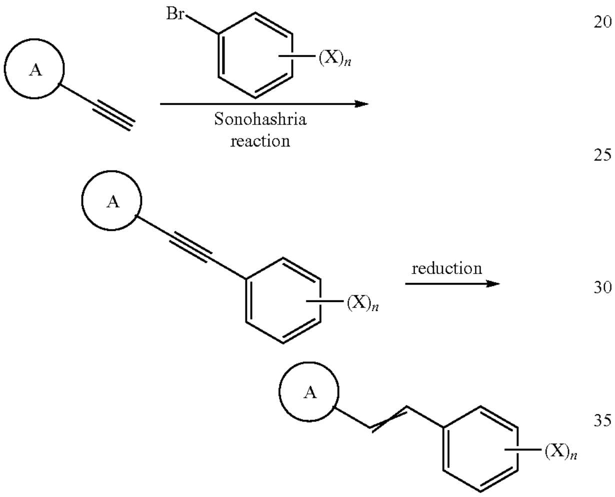

Scheme 2; General schemes for the synthesis of compounds of formula (II)

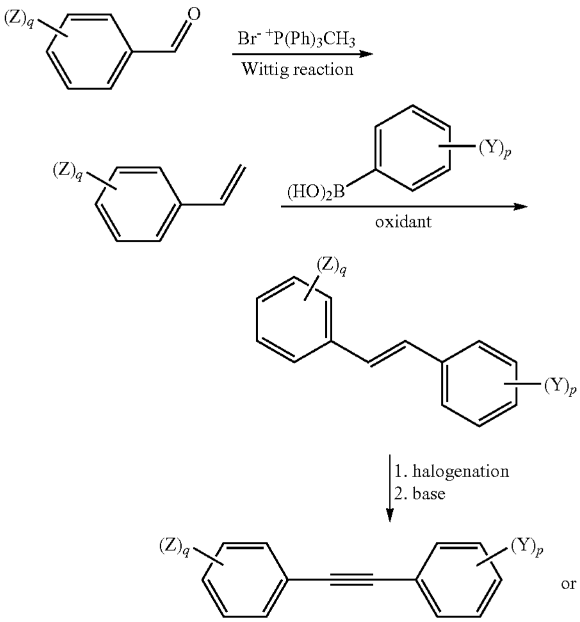

or

-continued

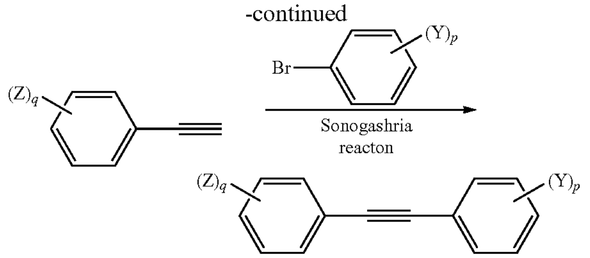

Scheme 3: General scheme for the synthesis of compounds of formula (III)

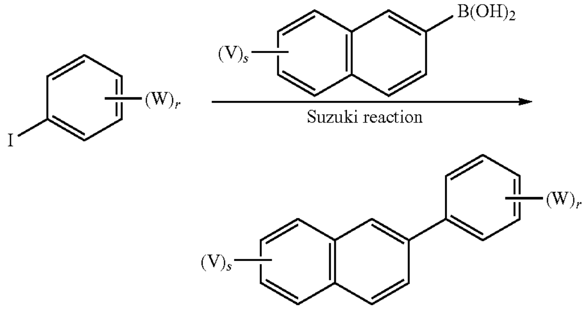

Scheme 4: General scheme for the synthesis of compounds of formula (IV)

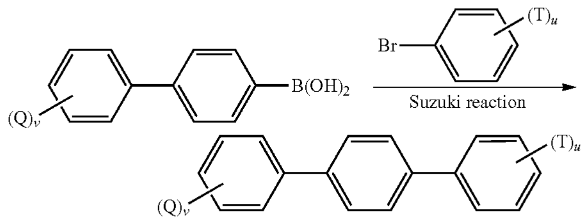

Any method for the preparation of a compound of formula (I), (II), (III) or (IV) which comprises the step of deprotecting a protected derivative thereof also forms part of the invention.

The compounds herein described have valuable pharmacological properties. Specifically, these have an inhibitory effect on the synthesis of glutathione (GSH), an anti-oxidant which constitutes a major defence system against reactive oxygen species in mammalian cells. In view of their ability to inhibit GSH production, the compounds herein disclosed are capable of increasing oxidative stress during radiotherapy thereby overcoming radio-resistance in the treatment of cancer.

For use in such treatment, a therapeutically effective amount of the compound (i.e. an amount sufficient to radiosensitize cells in tumours) is administered to tumour cells in the selected subject (e.g. a human patient) in combination with radiotherapy. The combined administration of the compound and radiation treatment are carried out sufficiently closely in time that the presence of the compound potentiates the radiation treatment. The tumour cells may be subjected to radiotherapy before, during or after administration of any of the compounds herein described. Simultaneous administration may be carried out by administering the selected compound and delivering the radiation treatment at the same point in time. Sequential administration may be carried out by administering the selected compound and radiation treatment at a different point in time. For example, an active compound as described herein may be administered orally, or parenterally (e.g. intravenousy) to a patient prior to receiving radiation therapy. In some embodiments, the treatment regimen may comprise a first step of administering the active compound herein described to the subject (e.g. human patient), followed by exposure of the subject to radiation therapy.

Any known method of radiotherapy may be used in combination with administration of the radiosensitizer compounds herein described. In one embodiment, the radiosensitizer may be administered in combination with fractionated radiotherapy (FR). With fractionation, the total radiation dose is divided into smaller doses administered over several days. This regimen reduces toxicity by giving healthy cells time to repair radiation damage between each fraction, whilst retaining anti-tumour efficacy as tumour cells have less effective repair systems. This is a standard treatment for numerous cancer types and may, for example, involve a total dose of up to 60 Gy divided in up to 30 fractions of 2 Gy over a 6 week course (2 Gy every day except weekends). In other embodiments, the radiosensitizer may be combined with a single session radiation treatment in which the whole radiation dose is administered in one session but with focal beams/stereotactic technique to spare surrounding healthy tissue. Such treatment regimens are used with gamma knife and x-knife treatment.

Any known source of ionizing radiation may be used in the invention. The source of ionizing radiation may, for example, be a linear particle accelerator (linac) that creates X-rays, gamma rays generated from radioactive cobalt in the gamma knife, or ionizing radiation created by proton beams (proton therapy).

Radiation treatment may be given for metastatic disease in the advanced stage, pre-operatively to shrink the primary tumour before surgery, or post-operatively when tumour cells have been detected in lymph nodes harvested during surgery.

Cancers which may benefit from treatment in accordance with the invention include any radio-resistant cancers. For example, the cancer may be one selected from any of the following: malignant gliomas, medulloblastoma, neuroblastoma, Kaposi's sarcoma, head and neck squamous cell carcinoma, tongue cancer, esophageal squamous cell carcinoma, thyroid cancer, melanoma, breast cancer, prostate cancer, laryngeal squamous cell carcinoma, lung cancer, mesothelioma, gastric cancer, hepatocellular carcinoma, pancreatic cancer, cholangiocarcinoma, colon cancer, renal cancer, urothelial cancer, testis cancer, endometrial cancer, ovarian cancer, cervical cancer, and metastases from any of these cancers, as well as myeloma, lymphoma and leukemia. In one embodiment, the cancer is GBM, breast or lung cancer. Treatment of GBM is a preferred embodiment of the invention.

In a further aspect the invention thus provides a compound of general formula (I), (II), (III) or (IV) as herein described, a stereoisomer or a pharmaceutically acceptable salt thereof for use in therapy or for use as a medicament.

In another aspect the invention provides the use of a compound of general formula (I), (II), (III) or (IV) as herein described, a stereoisomer or a pharmaceutically acceptable salt thereof in the manufacture of a medicament for use as a radiosensitizer in the treatment of cancer.

Also provided is a method of treatment of a human or non-human animal body to combat cancer, said method comprising the step of administering to said body an effective amount of a compound of general formula (I), (II), (III) or (IV) as herein described, a stereoisomer or pharmaceutically acceptable salt thereof, in combination with radiotherapy. The patient may be a human.

For use in a therapeutic treatment, the compounds herein described may be administered alone or in combination with pharmaceutically acceptable carriers, excipients or diluents. Typically, these will be formulated as a pharmaceutical formulation.

In a further aspect, the invention thus provides a pharmaceutical composition comprising a compound of general formula (I), (II), (III) or (IV) as herein described, or a stereoisomer, or pharmaceutically acceptable salt thereof, together with one or more pharmaceutically acceptable carriers, excipients or diluents.

Acceptable carriers, excipients and diluents for therapeutic use are well known in the art and can be selected with regard to the intended route of administration and standard pharmaceutical practice. Examples include binders, lubricants, suspending agents, coating agents, solubilizing agents, preserving agents, wetting agents, emulsifiers, surfactants, sweeteners, colorants, flavoring agents, antioxidants, odorants, buffers, stabilizing agents and/or salts.

The compounds herein described may be formulated with one or more conventional carriers and/or excipients according to techniques well known in the art. Typically, the compositions will be adapted for oral or parenteral administration, for example by intradermal, subcutaneous, intraperitoneal or intravenous injection.

For example, these may be formulated in conventional oral administration forms, e.g. tablets, coated tablets, pills, hard or soft capsules, powders (e.g. reconstitutable powders), granulates, liquid preparations, aqueous or oily solutions, dispersions, aqueous or oily suspensions, syrups, elixirs, lozenges, emulsions, etc. using conventional excipients, e.g. solvents, diluents, binders, sweeteners, aromas, pH modifiers, viscosity modifiers, antioxidants, etc. Suitable excipients may include, for example, corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose or fatty substances such as saturated fats or suitable mixtures thereof, etc. Depending on the administration form, the product may be provided in the form of a sachet or vial containing the pharmaceutical composition.

Where parenteral administration is employed this may for example be by means of intravenous, subcutaneous or intramuscular injection. For this purpose, sterile solutions containing the active agent may be employed, such as an oil-in-water emulsion. Where water is present, an appropriate buffer system (e.g., sodium phosphate, sodium acetate or sodium borate) may be added to prevent pH drift under storage conditions.

The use of orally administrable compositions, e.g. tablets, coated tablets, capsules, syrups, etc. is especially preferred.

The formulations may be prepared using conventional techniques, such as dissolution and/or mixing procedures, tableting, etc.

The dosage required to achieve the desired activity of the compounds herein described will depend on various factors, such as the compound selected, its mode and frequency of administration, whether the treatment is therapeutic or prophylactic, and the nature and severity of the disease or condition, etc. Typically, a physician will determine the actual dosage which will be most suitable for an individual subject. The specific dose level and frequency of dosage for any particular patient may be varied and will depend upon factors such as the activity of the specific compound employed, the metabolic stability and length of action of that compound, the relation of potency to absorbability of the compound, the age of the patient, the mode and timing of administration, and the severity of the condition.

The pharmacological properties of the compounds herein described can be analysed using standard assays for functional activity. Examples of protocols for testing of the compounds are provided in the Examples.

The invention will now be described in more detail by way of the following non-limiting Examples and accompanying Figures, in which:

FIG. 1A—results of toxicity studies following in vivo administration of compound DC10 to mice in accordance with Example 21; and FIG. 1B—tumour volume in mice grafted with A375 melanoma cells following treatment in accordance with Example 21. "RT"=radiotherapy.

EXAMPLES

Example 1

Preparation of (E)-2-methoxy-5-styrylbenzoic acid—DC01

1.1 Preparation of 3-bromo-4-hydroxybenzaldehyde (1)

A mixture of 4-hydroxybenzaldehyde (5.0 g, 40.94 mmol) in acetonitrile (25 mL) was cooled at 0° C. p-Toluenesulfonic acid monohydrate (1.1 eq., 8.57 g, 45.04 mmol) and N-bromosuccinimide (1.1 eq., 8.02 g, 45.04 mmol) were then added. The reaction mixture was stirred overnight at room temperature using a flask wrapped in aluminum foil. The reaction was monitored by TLC using an eluent containing hexane:ethyl acetate=8:2. The solvent was removed under reduced pressure, whereupon the crude was diluted with DCM and a saturated solution of $Na_2S_2O_3$ in water and the aqueous phase were extracted two more times with DCM. The organic phases were reunited, dried over $Na_2SO_4$ anhydrous and concentrated under reduced pressure to afford the desired compound 1 (7.1 g, 35.32 mmol) as a yellow oil and with a yield of 86%.

$^1$H NMR (400 MHz, DMSO) δ 10.70 (s, 1H), 9.68 (s, 1H), 7.89 (d, J=2.0 Hz, 1H), 7.58 (dd, J=8.3, 2.0 Hz, 1H), 7.00 (d, J=8.3 Hz, 1H). $^{13}$C NMR (101 MHz, $CDCl_3$) δ 188.84, 159.44, 134.28, 130.16, 129.16, 129.13, 116.00, 110.14.

1.2 Preparation of 3-bromo-4-methoxybenzaldehyde (2a)

3-Bromo-4-hydroxybenzaldehyde 1 (7.0 g, 34.82 mmol) in acetone (25 mL) was added to $Na_2CO_3$ (2 eq., 7.38 g, 69.65 mmol) and iodomethane (2 eq., 9.89 g, 4.34 mL, 69.65 mmol). The reaction mixture was stirred at 20° C. for 18 h. The progress of the reaction was monitored by TLC, using hexane:ethyl acetate=9:1 as eluent. The solvent was removed under reduced pressure and the mixture was extracted with DCM (3×250 mL). The organic phases were combined, dried over anhydrous $Na_2SO_4$ and concentrated under reduced pressure to obtain target compound 2a (7.03 g, 32.69 mmol) as a yellow oil in a yield of 94%.

$^1$H NMR (500 MHz, $CDCl_3$) δ 9.75 (s, 1H), 8.24 (d, J=2.0 Hz, 1H), 7.79 (dd, J=8.5, 2.0 Hz, 1H), 6.86 (d, J=8.5 Hz, 1H), 3.91 (s, 3H). $^{13}$C NMR (126 MHz, Acetone) δ 190.34, 161.50, 134.71, 132.12, 132.07, 113.25, 112.76, 57.23.

1.3 Preparation of 3-bromo-4-(methoxymethoxy)benzaldehyde (2b)

3-Bromo-4-hydroxybenzaldehyde 1 (7.0 g, 34.82 mmol) in DCM (25 mL) that was cooled at 0° C. was added to N,N-Dicyclohexylmethylamine (2 eq., 13.61 g, 14.92 mL, 69.65 mmol) and chloromethyl methyl ether (1.5 eq., 4.21 g, 3.97 mL, 52.23 mmol). The reaction mixture was stirred at 20° C. for 18 h. The progress of the reaction was monitored by TLC, using hexane:ethyl acetate=9:1 as eluent. The reaction mixture was poured in HCl (0.1 M) and then extracted with DCM (3×250 mL). The organic phases were combined, dried over anhydrous $Na_2SO_4$, and concentrated under reduced pressure. The white solid obtained was filtered and washed with $Et_2O$. The filtrated was collected and concentrated under reduced pressure to afford the desired compound 2b (8.15 g, 33.26 mmol) as a yellow oil and with a yield of 95%.

$^1$H NMR (500 MHz, $CDCl_3$) δ 9.86 (s, 1H), 8.09 (d, J=2.0 Hz, 1H), 7.79 (dd, J=8.5, 2.0 Hz, 1H), 7.27 (d, J=8.5 Hz, 1H), 5.35 (s, 2H), 3.53 (s, 3H). $^{13}$C NMR (126 MHz, $CDCl_3$) δ 189.55, 158.42, 134.47, 131.45, 130.81, 115.06, 113.33, 94.79, 56.62.

1.4 Preparation of benzyltriphenylphosphonium chloride (3)

Benzyl chloride (1.1 eq., 5.31 g, 1.10 mL, 41.94 mmol) was added to a solution of triphenylphosphine (10.0 g, 38.13 mmol) in toluene (25 mL) that was flushed with $N_2$, heated at reflux, and stirred overnight. A white precipitate was filtered off using hot toluene and the afforded solid was concentrated under reduced pressure. The desired compound 3 (14.60 g, 37.54 mmol) was produced as a white solid and with a yield of 98%.

$^1$H NMR (500 MHz, $CDCl_3$) δ 7.74-7.64 (m, 9H), 7.59-7.50 (m, 6H), 7.18-7.11 (m, 1H), 7.08-7.00 (m, 4H), 5.46 (d, J=14.5 Hz, 2H).

1.5 Preparation of (E)-2-bromo-1-methoxy-4-styrylbenzene (4)

KOH (1.2 eq., 219 mg, 3.91 mmol) was added to a solution of benzyltriphenylphosphonium chloride 3 (1.2 eq., 1.52 g, 3.91 mmol) in DCM (10 mL). Then, after a period of 30 min., 3-bromo-4-methoxybenzaldehyde 2a (700 mg, 3.26 mmol) was added to the mixture. The reaction mixture was stirred for 3 h at room temperature. The reaction was monitored by means of TLC using an eluent composed of hexane:ethyl acetate=9:1. The reaction crude obtained was filtered and washed with $Et_2O$. The filtrate was collected and concentrated under reduced pressure. To the crude, containing a mixture of the E and Z isomers, was added $I_2$ (1%, 8 mg, 32.55 μmol) using as solvent a mixture of hexane and EtOAc (8:2 ratio). The reaction was kept under stirring overnight 65° C. The mixture was extracted with ethyl acetate (3×50 mL) from a saturated $Na_2S_2O_3$ (aq) (50 mL), dried over anhydrous $Na_2SO_4$, filtered, and solvent evaporated under reduced pressure. The crude was re-crystallised in hexane. The desired product 4 (456 mg, 1.58 mmol) was obtained as a white solid with a yield of 48%.

$^1$H NMR (500 MHz, $CDCl_3$) δ 7.61 (d, J=2.2 Hz, 1H), 7.39-7.33 (m, 2H), 7.24 (dt, J=9.4, 5.0 Hz, 3H), 7.19-7.10 (m, 1H), 6.84 (s, 2H), 6.73 (d, J=8.5 Hz, 1H), 3.76 (s, 3H).

$^{13}$C NMR (126 MHz, $CDCl_3$) δ 155.36, 137.18, 131.64, 131.01, 128.71, 127.99, 127.60, 126.87, 126.77, 126.39, 112.10, 111.94, 56.34.

1.6 Preparation of (E)-2-bromo-1-(methoxymethoxy)-4-styrylbenzene (5)

Benzyltriphenylphosphonium chloride 3 (1.2 eq., 1.33 g, 3.43 mmol) was dissolved in DCM (10 mL) using a reaction flask (25 mL), The mixture was then added to KOH (1.2 eq., 192 mg, 3.43 mmol) and after 30 min., 3-bromo-(4-methoxymethoxy) benzaldehyde 2b (700 mg, 2.86 mmol) was also added to the solution. The reaction mixture is stirred for 3 h at room temperature. The reaction was monitored by TLC, using as eluent hexane/EtOAc 9:1. The reaction crude obtained was filtered and washed with $Et_2O$. The filtrate was collected and concentrated under reduced pressure. To the crude, containing a mixture of the E and Z isomers was added $I_2$ (1%, 7 mg, 28.56 μmol) using as solvent a mixture of hexane and ethyl acetate=8:2. The reaction was stirred overnight at 65° C. The mixture was extracted from a saturated water solution of $Na_2S_2O_3$ with ethyl acetate (3×250 mL), dried over $Na_2SO_4$ and purified through silica gel column chromatography (hexane/EtOAc 99.5:0.5). The desired product 5 (398 mg, 1.25 mmol) was obtained as a yellow oil with a yield of 43%.

$^1$H NMR (500 MHz, $CDCl_3$) δ 7.71 (d, J=2.1 Hz, 1H), 7.48-7.44 (m, 2H), 7.37-7.30 (m, 3H), 7.27-7.21 (m, 1H), 7.10 (d, J=8.5 Hz, 1H), 6.96 (s, 2H), 5.23 (s, 2H), 3.51 (s, 3H). $^{13}$C NMR (126 MHz, $CDCl_3$) δ 153.18, 137.11, 132.89, 131.06, 128.75, 128.47, 127.73, 126.75, 126.70, 126.49, 116.13, 113.26, 95.14, 56.45

1.7 Preparation of (E)-2-methoxy-5-styrylbenzoic acid (DC01)

THF anhydrous (6 mL) was added in a Schlenk flask containing Mg (5 eq., 63 mg, 2.59 mmol), followed by the addition of dibromoethane (2 eq., 195 mg, 89 μL, 1.04 mmol). After 10 min., compound 4 (150 mg, 519 μmol) was added in the mixture. The reaction was kept overnight under stirring at reflux. Afterwards, $CO_2$ was bubbled for 10 min. through the reaction by means of a gas diffuser. The post-reaction mixture was acidified and extracted with DCM (3×50 mL). The organic phases were combined, dried over anhydrous $Na_2SO_4$, filtered, and concentrated under reduced pressure. The crude was purified through silica gel column chromatography (DCM/MeOH 95:5). Target molecule DC01 (53 mg, 208 μmol) was isolated as a white solid with a yield of 40%.

$^1$H NMR (500 MHz, $CDCl_3$) δ 8.37 (d, J=2.4 Hz, 1H), 7.69 (dd, J=8.6, 2.4 Hz, 1H), 7.51 (dd, J=7.3, 1.2 Hz, 2H), 7.39-7.34 (m, 2H), 7.30-7.27 (m, 1H), 7.15-7.04 (m, 3H), 4.11 (s, 3H). $^{13}$C NMR (126 MHz, $CDCl_3$) δ 165.14, 157.18, 136.89, 132.82, 132.02, 131.50, 129.32, 128.77, 127.90, 126.53, 126.30, 117.80, 112.03, 56.92.

HR-MS (ESI): $[M+H]^+$: Calcd for $C_{16}H_{15}O_3$ 255.10212, found 255.10237 and $[M+Na]^+$: Calcd for $C_{16}H_{14}NaO_3$ 277.08406, found 277.08412.

Example 2

Preparation of (E)-2-hydroxy-5-styrylbenzoic acid—DC02

THF anhydrous (6 mL) was added in a Schlenk flask containing Mg (5 eq., 57 mg, 2.35 mmol), followed by the addition of dibromoethane (2 eq., 177 mg, 81 μL, 940 μmol). After 10 min., compound 5 (150 mg, 470 μmol) was added in the mixture. The reaction was kept overnight under stirring at reflux. Afterwards, $CO_2$ was bubbled for 10 min. through the reaction by means of a gas diffuser. The reaction mixture was extracted with DCM (3×50 mL). The organic phases were reunited, dried over $Na_2SO_4$ anhydrous and concentrated under reduced pressure. The crude was purified through silica gel column chromatography (DCM/MeOH 9:1). The desired product DC02 (51 mg, 212 μmol) was obtained as a white solid with a yield of 45%.

$^1$H NMR (500 MHz, $CD_3CN$) δ 8.05 (d, J=1.7 Hz, 1H), 7.79 (dd, J=8.6, 2.0 Hz, 1H), 7.58 (d, J=7.6 Hz, 2H), 7.40 (t, J=7.6 Hz, 2H), 7.29 (t, J=7.3 Hz, 1H), 7.16 (dd, J=37.0, 16.5 Hz, 2H), 7.01 (d, J=8.7 Hz, 1H). $^{13}$C NMR (126 MHz, $CD_3CN$) δ 171.30, 161.22, 137.19, 132.96, 128.61, 128.39, 128.32, 127.14, 126.92, 126.84, 125.96, 117.39 (one carbon peak under solvent peak).

HR-MS (ESI): $[M-H]^-$: Calcd for $C_{15}H_{11}O_3$ 239.07082, found 239.07055

Example 3

Preparation of (Z)-2-methoxy-5-styrylbenzoic acid—DC03

3.1 Preparation of 2-bromo-4-iodophenol (6)

To a solution of 4-iodophenol (5.0 g, 22.73 mmol) in acetonitrile (25 mL) cooled at 0° C. was added first p-toluenesulfonic acid monohydrate (1.1 eq., 4.76 g, 25.00 mmol) and then N-bromosuccinimide (1.1 eq., 4.45 g, 25.00 mmol). The reaction mixture was stirred overnight at room temperature and the flask was wrapped in aluminum foil. The reaction was monitored by TLC, using as eluent hexane: ethyl acetate=8:2. The solvent was removed under reduced pressure. The crude was diluted with DCM and a saturated solution of $Na_2S_2O_3$ in water and the aqueous phase was extracted two more times with DCM. The organic phases were reunited, dried over $Na_4SO_4$ anhydrous and concentrated under reduced pressure to afford the desired compound 6 (6.25 g, 20.91 mmol) as a yellow solid and with a yield of 92%.

$^1$H NMR (500 MHz, $CDCl_3$) δ 7.75 (d, J=1.7 Hz, 1H), 7.49 (dd, J=8.6, 1.7 Hz, 1H), 6.78 (d, J=8.8 Hz, 1H), 4.53 (s, 1H). $^{13}$C NMR (126 MHz, $CDCl_3$) δ 152.34, 139.64, 138.04, 118.12, 111.34, 82.02

3.2 Preparation of 2-bromo-4-iodo-1-methoxybenzene (7a)

$Na_2CO_3$ (2 eq., 4.26 g, 40.15 mmol) and iodomethane (2 eq., 5.70 g, 2.50 mL, 69.65 mmol) were added to a solution of 2-bromo-4-iodophenol 6 (6.0 g, 20.07 mmol) in acetone (25 mL). This reaction mixture was stirring for 20 hrs at a temperature 20° C. The reaction was monitored by TLC using an eluent composed of hexane:ethyl acetate=9:1. The solvent was removed under reduced pressure and the mixture was extracted (3×250 mL) with DCM from water. The organic phases were combined and dried over anhydrous $Na_2SO_4$, filtered, and concentrated under reduced pressure to afford target compound 7a (5.91 g, 18.89 mmol) as a yellow oil and with a yield of 94%.

$^1$H NMR (500 MHz, $CDCl_3$) δ 7.82 (d, J=2.1 Hz, 1H), 7.54 (dd, J=8.7, 2.1 Hz, 1H), 6.65 (d, J=8.6 Hz, 1H), 3.87 (s,

3H). $^{13}C$ NMR (126 MHz, $CDCl_3$) δ 155.98, 140.99, 137.27, 113.84, 112.96, 82.44, 56.31.

3.3 Preparation of 2-bromo-4-iodo-14methoxymethoxy)benzene (7b)

N,N-Dicyclohexylmethylamine (2 eq., 7.84 g, 8.60 mL, 40.15 mmol) and then chloromethyl methyl ether (1.5 eq., 2.42 g, 2.29 mL, 30.11 mmol) were added to a cold (0° C.) solution of 2-bromo-4-iodophenol 6 (6.0 g, 20.07 mmol) in DCM (25 mL). This reaction mixture was stirred for 18 h at a temperature of 20° C. The reaction mixture was monitored by TLC by using as eluent hexane:ethyl acetate=9:1. The reaction mixture was poured in HCl 0.1 M and extracted with DCM (3×250 mL). The organic phases were combined, dried over anhydrous $Na_2SO_4$ and concentrated under reduced pressure. The white solid obtained was filtered and washed with $Et_2O$. The filtrate was collected and concentrated under reduced pressure to afford the desired compound 7b (6.20 g, 18.08 mmol) as a yellow oil and with a yield of 90%.

$^1H$ NMR (500 MHz, $CDCl_3$) δ 7.84 (d, J=2.1 Hz, 1H), 7.52 (dd, J=8.7, 2.1 Hz, 1H), 6.91 (d, J=8.7 Hz, 1H), 5.22 (s, 2H), 3.50 (s, 3H). $^{13}C$ NMR (126 MHz, $CDCl_3$) δ 153.85, 141.12, 137.29, 117.87, 114.06, 95.06, 84.21, 56.45.

3.4 Preparation of 2-bromo-1-methoxy-4-(phenylethynyl)benzene (8)

Phenylacetylene (1.1 eq., 373 mg, 401 μL, 3.66 mmol), 7 (1.04 g, 3.32 mmol) and diethylamine (5 mL) were transferred to a round bottom flask (50 mL) under an argon atmosphere. This mixture was poured into another round bottom flask (50 mL) containing a mixture of $Pd(PPh_3)_4$ (3%, 115 mg, 100 μmol) and CuI (10%, 63 mg, 332 μmol) in toluene (6 mL). The mixture was heated at 50° C. and stirred for 1 h. The reaction was monitored by TLC, using as eluent hexane:ethyl acetate=9:1. The solvent was then removed under reduced pressure and the mixture was extracted with DCM (3×250 mL) from water. The organic phases were combined, dried over anhydrous $Na_2SO_4$ and concentrated under reduced pressure to afford target compound 8 (811 mg, 2.82 mmol) as an off-white solid and with a yield of 85%.

$^1H$ NMR (500 MHz, $CDCl_3$) δ 7.74 (d, J=2.1 Hz, 1H), 7.52-7.49 (m, 2H), 7.45 (dd, J=8.5, 2.0 Hz, 1H), 7.36-7.32 (m, 3H), 6.87 (d, J=8.5 Hz, 1H), 3.92 (s, 3H). $^{13}C$ NMR (126 MHz, $CDCl_3$) δ 156.03, 136.29, 132.00, 131.52, 128.37, 128.26, 123.14, 116.89, 111.57, 111.43, 89.07, 87.81, 56.31.

3.5 Preparation of (Z)-2-bromo-1-methoxy-4-styrylbenzene (9)

2-Bromo-1-methoxy-4-(phenylethynyl)benzene 8 (350 mg, 1.22 mmol) in ethylacetate (10 mL) was transferred to a round bottom flask (25 mL) wrapped with aluminum foil. Quinoline (0.4 eq., 63 mg, 58 μL, 487 μmol) and the Lindlar catalyst 5% Pd w/w (380 mg, 15% Pd eq.) were then added. The reaction mixture was stirred under a $H_2$ atmosphere at a temperature of 40° C. for 18 h. The reaction mixture was monitored by TLC using hexane:ethyl acetate=9:1 as the eluent. The solvent was then removed under reduced pressure and the mixture was extracted with DCM (3×50 mL). The organic phases were combined, dried over anhydrous $Na_2SO_4$, concentrated under reduced pressure, and purified through silica gel column chromatography (hexane:ethyl acetate 99.5:0.5). Target compound 9 (288 mg, 996 μmol) was obtained as a yellow solid in a yield of 81%.

$^1H$ NMR (500 MHz, $CDCl_3$) δ 7.43 (d, J=2.0 Hz, 1H), 7.26-7.18 (m, 5H), 7.13 (dd, J=8.6, 2.1 Hz, 1H), 6.72 (d, J=8.5 Hz, 1H), 6.55 (d, J=12.2 Hz, 1H), 6.45 (d, J=12.2 Hz, 1H), 3.85 (s, 3H). $^{13}C$ NMR (126 MHz, $CDCl_3$) δ 154.91, 137.07 133.78, 131.15, 130.12, 129.09, 128.84, 128.40, 128.37, 127.31, 111.54, 111.31, 56.21.

3.6 Preparation of (Z)-2-methoxy-5-styrylbenzoic acid (DC03)

Mg (5 eq., 63 mg, 2.59 mmol) was transferred to a Schlenk flask (100 mL) together with anhydrous THF (6 mL). Then, dibromoethane (2 eq., 195 mg, 89 μL, 1.04 mmol) was added to the reaction mixture. After a short period of time (≈10 min.), (Z)-2-bromo-1-methoxy-4-styrylbenzene 9 (150 mg, 519 μmol) was added to the reaction mixture. The reaction mixture was stirred continuously at reflux for another 18 h. Then $CO_2$ was bubbled by means of a gas diffuser (porous glass sinter at the tip of the glass tube) through the reaction mixture for a period of 10 min. The reaction mixture was extracted with DCM (3×50 mL). The organic phases were combined, dried over anhydrous $Na_2SO_4$, and concentrated under reduced pressure. The crude was purified using a silica gel chromatography column (DCM:MeOH=95:5). Target product DC03 (60 mg, 236 μmol) was obtained as a transparent oil with a yield of 45%.

$^1H$ NMR (500 MHz, $CDCl_3$) δ 8.05 (d, J=2.3 Hz, 1H), 7.39 (dd, J=8.7, 2.3 Hz, 1H), 7.26-7.16 (m, 5H), 6.84 (d, J=8.7 Hz, 1H), 6.63 (d, J=12.1 Hz, 1H), 6.53 (d, J=12.2 Hz, 1H), 4.01 (s, 3H). $^{13}C$ NMR (126 MHz, $CDCl_3$) δ 165.54, 156.98, 136.72, 135.05, 134.29, 131.23, 130.81, 128.63, 128.33, 128.02, 127.28, 117.40, 111.42, 56.62. HR-MS (ESI): $[M+H]^+$: Calcd for $C_{16}H_{15}O_3$ 255.10212, found 255.10103

Example 4

Preparation of 2-methoxy-5-(phenylethynyl)benzoic acid—DC04

Mg (5 eq., 63 mg, 2.61 mmol) and anhydrous THF (6 mL) were transferred to a Schlenk flask (100 mL) whereupon dibromoethane (2 eq., 196 mg, 90 μL, 1.04 mmol) was added. Then, after a period of ≈10 min., 2-bromo-1-methoxy-4-(phenylethynyl)benzene 8 (150 mg, 522 μmol) was added to the mixture. The reaction mixture was continuously stirred at reflux for a period of 18 h. Then, $CO_2$ was bubbled through the reaction mixture by means of a gas diffuser (porous glass sinter at the tip of the glass tube) through the reaction mixture for a period of 10 min. The reaction mixture was extracted with DCM (3×50 mL). The organic phases were combined, dried over anhydrous $Na_2SO_4$ and concentrated under reduced pressure. The crude was purified through column chromatography using silica gel using an eluent composed by DCM:methanol=95:5. The desired product DC04 (63 mg, 249 μmol) was obtained as a transparent oil in a yield of 48%.

$^1H$ NMR (500 MHz, $CDCl_3$) δ 8.36 (d, J=2.1 Hz, 1H), 7.71 (dd, J=8.6, 2.2 Hz, 1H), 7.57-7.48 (m, 2H), 7.39-7.32 (m, 3H), 7.05 (d, J=8.6 Hz, 1H), 4.10 (s, 3H). $^{13}C$ NMR (126 MHz, $CDCl_3$) δ 164.68, 157.62, 137.74, 137.09, 131.57, 128.47, 128.39, 122.84, 117.89, 117.72, 111.91, 89.76, 87.36, 56.90. HR-MS (ESI): $[M+H]^+$: Calcd for $C_{16}H_{13}O_3$ 253.08647, found 253.08677.

Example 5

Preparation of 2-methoxy-5-(naphthalen-2-yl)benzoic acid—DC05

5.1 Preparation of 2-(3-bromo-4-methoxyphenyl)naphthalene (10)

2-Bromo-4-iodo-1-methoxybenzene 7a (1 g, 3.20 mmol), naphthalen-2-ylboronic acid (1 eq., 550 mg, 3.20 mmol), $K_2CO_3$ (2 eq., 883 mg, 6.39 mmol), $Pd(PPh_3)_4$ (5%, 158 mg, 160 μmol), and DMF (10 mL) were transferred to a round bottom flask (50 mL). This reaction mixture was flushed with argon and then continuously stirred for 2 h at 100° C. The reaction mixture was monitored by TLC using an eluent composed of hexane:ethyl acetate=9:1. The solvent was removed from the post reaction mixture under reduced pressure and then extracted with DCM (3×100 mL). The organic phases were combined, dried over anhydrous $Na_2SO_4$, concentrated under reduced pressure, and purified through silica gel chromatography column (hexane:ethyl acetate=99.5:0.5). Target compound 10 (734 mg, 2.34 mmol) was obtained as a yellow solid in a yield of 73%.

$^1H$ NMR (500 MHz, $CDCl_3$) δ 7.81 (s, 1H), 7.79 (d, J=2.2 Hz, 1H), 7.72 (dd, J=12.9, 7.6 Hz, 3H), 7.51 (dd, J=8.5, 1.8 Hz, 1H), 7.44 (dd, J=8.5, 2.2 Hz, 1H), 7.39-7.32 (m, 2H), 6.80 (d, J=8.5 Hz, 1H), 3.77 (s, 3H). $^{13}C$ NMR (126 MHz, $CDCl_3$) δ 155.42, 136.73, 135.02, 133.72, 132.57, 132.12, 128.61, 128.19, 127.71, 127.34, 126.46, 126.03, 125.30, 125.13, 112.22, 56.37 (one carbon peak is not visible)

5.2 Preparation of 2-methoxy-5-(naphthalen-2-yl)benzoic acid (DC05)

Oxalic acid (3 eq, 86 mg, 958 μmol), $Pd(OAc)_2$ (5%, 4 mg, 16 μmol), Xantphos (5%, 9 mg, 16 μmol), 2-(3-bromo-4-methoxyphenyl)naphthalene 10 (100 mg, 319 μmol) and DMF (5 mL) were transferred to a glass tube reactor, that was sealed and left under stirring in an oil bath at 100° C. The septum was penetrated with a syringe needle that was attached to a balloon (for pressure equalization during the in-situ CO production) and TEA (3 eq., 97 mg, 134 μL, 958 μmol) was added. Then $Ac_2O$ (3 eq., 98 mg, 90 μL, 958 μmol) was drop-wise added over a period of 15 min. by means of a syringe pump. During the $Ac_2O$ addition, CO was formed, though the decomposition of oxalic acid. The reaction mixture was stirred at 100° C. for 3 h. The post reaction mixture was extracted with DCM (3×50 mL). The organic phases were combined, dried over anhydrous $Na_2SO_4$, and concentrated under reduced pressure. The isolated crude product was purified by means of a chromatography column filled with silica gel with an eluent composed of DCM:methanol=95:5). Target product DC05 was obtained as a white solid with a yield of 57% (51 mg, 183 μmol).

$^1H$ NMR (500 MHz, $CDCl_3$) δ 10.70 (s, 1H), 8.57 (s, 1H), 8.04 (s, 1H), 7.96-7.82 (m, 4H), 7.73 (d, J=8.5 Hz, 1H), 7.50 (t, J=6.8 Hz, 2H), 7.17 (d, J=8.6 Hz, 1H), 4.13 (s, 3H). $^{13}C$ NMR (126 MHz, $CDCl_3$) δ 165.42, 157.45, 136.20, 135.32, 133.64, 133.57, 132.69, 132.43, 128.70, 128.20, 127.66, 126.52, 126.20, 125.59, 124.92, 117.95, 112.28, 56.94. HR-MS (ESI): $[M+H]^+$: Calcd for $C_{18}H_{13}O_3$ 277.08647, found 277.08678.

Example 6

Preparation of (E)-5-(4-fluorostyryl)-2-hydroxybenzoic acid—DC07

6.1 Preparation of methyltriphenylphosphonium iodide (11)

Iodomethane (1.1 eq., 11.91 g, 5.22 mL, 83.88 mmol) was added to a solution of triphenylphosphine (20.0 g, 76.25 mmol) in THF (25 mL). The reaction was flushed with $N_2$, heated at reflux and continuously stirred for 18 h. A white precipitate that was formed was filtered off and the afforded solid was concentrated under reduced pressure. Target compound 11 was isolated as a white solid in a yield of 93% (28.60 g, 70.75 mmol).

$^1H$ NMR (500 MHz, $CDCl_3$) δ 7.85-7.67 (m, 15H), 3.22 (d, J=13.2 Hz, 3H).

6.2 Preparation of 2-bromo-1-(methoxymethoxy)-4-vinylbenzene (12)

At 0° C., compound 11 (1.2 eq., 3.96 g, 9.79 mmol) was slowly added to a suspension of NaH 60% (3 eq., 979 mg, 24.48 mmol) in anhydrous DCM (15 mL). The mixture was then left for stirring in 30 min., whereupon compound 2b (2.0 g, 8.16 mmol) was added to the mixture. The mixture was then stirred for 16 h at 20° C. The reaction mixture was then quenched with a saturated solution of $NaHCO_3$ in water. The quenched post-reaction mixture was then extracted with DCM (3×250 mL). The combined organic layers were dried over $Na_2SO_4$, and then purified using column chromatography filled with silica gel (eluent hexane: ethyl acetate=9:1), which afforded the target compound 12 (1.76 g, 7.24 mmol) as a transparent oil in a yield of 89%.

$^1H$ NMR (500 MHz, $CDCl_3$) δ 7.61 (d, J=2.1 Hz, 1H), 7.27 (dd, J=8.5, 2.1 Hz, 1H), 7.10 (d, J=8.5 Hz, 1H), 6.60 (dd, J=17.6, 10.9 Hz, 1H), 5.64 (d, J=17.3 Hz, 1H), 5.24 (s, 2H), 5.20 (d, J=10.7 Hz, 1H), 3.52 (s, 3H). $^{13}C$ NMR (126 MHz, $CDCl_3$) δ 153.29, 134.95, 133.10, 130.91, 126.38, 115.97, 113.57, 113.05, 95.11, 56.39.

6.3 Preparation of (E)-2-bromo-4-(4-fluorostyryl-1-(methoxymethoxy)benzene (13)

Method A: 1-fluoro-4-vinylbenzene (106 mg, 867.84 μmol), $Pd(OAc)_2$ (8%, 16 mg, 69 μmol), $K_2CO_3$ (2 eq., 240 mg, 21.74 mmol), compound 7b (1 eq., 297 mg, 867.84 μmol) and DMF (6 mL) were transferred to a reactor tube that was sealed. The mixture was flushed with Argon and sonicated for a period of 5 min. The reactor tube was immersed into the reactor cavity of a microwave oven at 100° C. for a period of 4 h. The progress of the reaction was monitored by TLC using an eluant composed of hexane: ethyl acetate=9:1. The solvent was removed under reduced pressure. The residue was then extracted with DCM (3×50 mL). The combined organic phases were dried over $Na_2SO_4$ and the solvent was removed under reduced pressure. The isolated crude product was purified using a chromatography column packed with silica gel using hexane:ethyl acetate=99:1 to achieve target compound 13 as a clear liquid in a yield of 35% (102 mg, 302.50 μmol).

Method B: 2-Bromo-1-(methoxymethoxy)-4-vinylbenzene 12 (210 mg, 867.84 μmol), 2,3-di(pyridin-2-yl)pyrazine (5%, 10 mg, 43 μmol), $Pd(OAc)_2$ (5%, 9 mg, 43 μmol), (4-fluorophenyl)boronic acid (1.1 eq., 133 mg, 950.23

μmol), $Cu(OAc)_2.H_2O$ (1.5 eq., 258 mg, 1.30 mmol), and 7 mL of DMF (7 mL) was transferred to a round bottom flask (50 mL). This mixture was continuously stirred for 18 h at 20° C. The course of the reaction was monitored by TLC, using hexane:ethyl acetate=9:1 as eluent. The post reaction mixture was added to a solution of EDTA in water (10 mL, 0.2 M) that was extracted with DCM (3×50 mL). The organic phases were combined, dried over anhydrous $Na_2SO_4$ and concentrated under reduced pressure. The mixture was purified using column chromatography packed with silica gel with hexane:ethyl acetate=99.6:0.4 as eluent. Target compound 13 was achieved as a clear liquid in a yield of 87% (254 mg, 753.29 μmol).

$^1$H NMR (500 MHz, $CDCl_3$) δ 3.36 (s, 3H), 5.07 (s, 2H), 6.65-6.77 (m, 2H), 6.82-6.91 (m, 3H), 6.95 (d, 1H), 7.14 (dd, 1H), 7.21-7.27 (m, 2H), 7.53 (d, 1H). $^{13}$C NMR (126 MHz, $CDCl_3$) δ 162.38 (d, J=247.1 Hz), 153.26, 133.32 (d, J=3.4 Hz), 132.68, 131.01, 127.97 (d, J=7.8 Hz), 127.17, 126.67, 126.47 (d, J=2.3 Hz), 116.07, 115.67 (d, J=21.8 Hz), 113.28, 95.09, 56.36.

6.4 Preparation of (E)-5-(4-fluorostyryl)-2-hydroxybenzoic acid (DC07)

Oxalic acid (3 eq, 360 mg, 4.00 mmol), $Pd(OAc)_2$ (5%, 15 mg, 66.73 μmol), Xantphos (5%, 39 mg, 66.73 μmol), 13 (450 mg, 1.33 mmol), water (10 eq., 240 mg, 13.35 mmol) and DMF (10 mL) were transferred to an reaction tube, that was sealed and left stirring in a preheated oil bath at 100° C. The septum was penetrated with a syringe needle that was attached to a balloon (for pressure equalization during the in-situ CO production). TEA (3 eq., 405 mg, 558 μL, 4.00 mmol) was then added, followed by an addition through a syringe pump over 15 min. of $Ac_2O$ (3 eq., 408 mg, 90 μL, 958 μmol). During the addition CO was formed though the degradation of the oxalic acid. The reaction was then stirred at 100° C. for 3 h. The reaction mixture was extracted with DCM (3×50 mL) from acid water. The organic phases were combined and dried over anhydrous $Na_2SO_4$, filtered and then concentrated under reduced pressure. The crude was purified through silica gel column chromatography (DCM/MeOH 95:5) to afford DC07 (163 mg, 0.631 mmol) with a yield of 47%.

$^1$H NMR (500 MHz, DMSO) δ 7.97 (d, J=2.3 Hz, 1H), 7.80 (dd, J=8.6, 2.2 Hz, 1H), 7.66-7.61 (m, 2H), 7.23-7.10 (m, 4H), 6.99 (d, J=8.6 Hz, 1H). $^{13}$C NMR (126 MHz, DMSO) δ 171.71, 161.45 (d, J=236.6 Hz), 160.84, 133.83, 132.82, 128.42, 128.20, 128.08 (d, J=7.3 Hz), 127.32, 125.48, 117.56, 115.51 (d, J=21.0 Hz), 113.61. HR-MS (ESI): $[M-H]^-$: Calcd for $C_{15}H_{10}FO_3$ 257.06149, found 257.06109.

Example 7

Preparation of (E)-2-hydroxy-5-(4-(methylthio)styryl)benzoic acid—DC08

7.1 Preparation of methyl(4-vinylphenyl)sulfane 14

Compound 11 (1.2 eq., 2.23 g, 5.52 mmol) was slowly added to a suspension of NaH 60% (3 eq., 551 mg, 13.80 mmol) in anhydrous DCM (10 mL) and left stirring for 30 min. at a temperature of at 0° C. 4-(Methylthio)benzaldehyde (700 mg, 4.60 mmol) was then added to the mixture and left stirring for 16 h at 20° C. The reaction mixture was quenched using a saturated solution of $NaHCO_3$ in water. The crude mixture was extracted with DCM (3×250 mL), dried over $Na_2SO_4$, and purified by means of column chromatography packed with silica gel (eluent hexane:ethyl acetate=9:1) to achieve target compound 14 (668 mg, 4.39 mmol) as a transparent oil in a yield of 95%.

$^1$H NMR (500 MHz, $CDCl_3$) δ 7.38-7.30 (m, 2H), 7.24-7.17 (m, 2H), 6.67 (dd, J=17.6, 10.9 Hz, 1H), 5.70 (dd, J=17.6, 0.7 Hz, 1H), 5.21 (dd, J=10.9, 0.7 Hz, 1H), 2.48 (s, 3H). $^{13}$C NMR (126 MHz, $CDCl_3$) δ 138.00, 136.20, 134,59, 126.63 (4C), 113.23, 15.86.

7.2 Preparation of (E)-(4-(3-bromo-4-(methoxymethoxy)styryl)phenyl)(methyl)sulfane (15)

Methyl(4-vinylphenyl)sulfane 14 (150 mg, 998.41 μmol), $Pd(OAc)_2$ (8%, 18 mg, 80 μmol), $K_2CO_3$ (2 eq., 276 mg, 2.00 mmol), 7b (1 eq., 342 mg, 998.41 μmol) and DMF (7 mL) were transferred to a sealed tube reactor. The tube reactor was flushed with Argon, sonicated for 5 min. and then immersed into the reactor cavity of a microwave oven that heated at 100° C. for 4 h. The progress of the reaction was monitored by TLC using hexane:ethyl acetate=9:1 as eluent. The solvent was removed under reduced pressure and the mixture was extracted with DCM (3×50 mL). The combined organic phases were dried over $Na_2SO_4$, filtered, and the solvent was removed under reduced pressure. The isolated crude was purified by means of column chromatography using silica gel with hexane:ethyl acetate=99:1 as eluent to obtain target compound 15 as a white solid in a yield of 44% (163 mg, 446.23 μmol).

$^1$H NMR (500 MHz, $CDCl_3$) δ 7.68 (d, J=2.1 Hz, 1H), 7.39-7.34 (m, 2H), 7.31 (dd, J=8.6, 2.1 Hz, 1H), 7.22-7.17 (m, 2H), 7.09 (d, J=8.5 Hz, 1H), 6.89 (s, 2H), 5.22 (s, 2H), 3.50 (s, 3H), 2.46 (s, 3H). $^{13}$C NMR (126 MHz, $CDCl_3$) δ 153.11, 138.03, 134.01, 132.89, 130.95, 127.79, 126.86, 126.67, 126.64, 126.03, 116.12, 113.26, 95.13, 56.43, 15.77.

7.3 Preparation of (E)-2-hydroxy-5-(4-(methylthio)styryl)benzoic acid (DC08)

Oxalic acid (3 eq, 59 mg, 0.657 mmol), $Pd(OAc)_2$ (5%, 3 mg, 10.95 μmol), Xantphos (5%, 6 mg, 10.95 μmol), 15 (80 mg, 0.219 mmol), water (10 eq., 40 mg, 2.19 mmol), and DMF (3 mL) were transferred to a reactor tube that was sealed and left for stirring in a preheated oil bath at 100° C. The septum was penetrated with a syringe needle that was attached to a balloon (for pressure equalization during the in-situ CO production). TEA (3 eq., 67 mg, 91 μL, 657 μmol) was then added. $Ac_2O$ (3 eq., 67 mg, 62 μL, 657 μmol)) was added over a period of over 15 min. by means of a syringe pump. During the addition CO was produced due to degradation of oxalic acid. The reaction mixture was stirred at 100° C. for 3 h. The reaction mixture was extracted DCM (3×50 mL) from acid water. The organic phases were combined, dried over anhydrous $Na_2SO_4$, filtered, and then concentrated under reduced pressure. The isolated crude was purified by means of a chromatography column packed with silica gel using DCM:methanol=95:5 as eluent to obtain title compound DC08 (37 mg, 0.129 mmol) as a white solid in a yield of 59%.

$^1$H NMR (500 MHz, DMSO) δ 7.96 (d, J=2.3 Hz, 1H), 7.80 (dd, J=8.7, 2.3 Hz, 1H), 7.56-7.49 (m, 2H), 7.28-7.23 (m, 2H), 7.20 (d, J=16.5 Hz, 1H), 7.09 (d, J=16.5 Hz, 1H), 6.98 (d, J=8.6 Hz, 1H), 2.49 (s, 3H). $^{13}$C NMR (126 MHz, DMSO) δ 171.72, 160.56, 137.16, 133.90, 132.96, 128.54, 128.32, 126.76, 126.55, 126.27, 126.08, 117.61, 113.18, 30.65. HR-MS (ESI): $[M-H]^-$: Calcd for $C_{16}H_{13}O_3S$ 285.05854, found 285.05887.

Example 8

Preparation of (E)-5-(2-([1,1'-biphenyl]-4-yl)vinyl)-2-hydroxybenzoic acid—DC10

8.1 Preparation of (E)-4-(3-bromo-4-(methoxymethoxy)styryl)-1,1'-biphenyl (16)

Compound 12 (500 mg, 2.81 mmol), 2,3-di(pyridin-2-yl) pyrazine (5%, 33 mg, 0.140 mmol), $Pd(OAc)_2$ (5%, 32 mg, 0.140 mmol), [1,1'-biphenyl]-4-ylboronic acid (1.1 eq., 611 mg, 3.09 mmol), and $Cu(OAc)_2$ monohydrate (1.5 eq., 764 mg, 4.21 mmol) in 10 mL of DMF were added to a flask (25 mL). The reaction mixture was stirred for 18 h at 20° C. and monitored by means of TLC using hexane:ethyl acetate=9:1 as eluent. The mixture was then extracted with DCM (3×100 mL) from a solution EDTA in water (0.2 M). The organic phases were combined, dried over anhydrous $Na_2SO_4$, filtered, and concentrated under reduced pressure. The mixture was purified by means of column chromatography packed with silica gel (eluent hexane:ethyl acetate=99.6 0.4). The target compound 16 (910 mg, 2.30 mmol) was isolated as a white solid in a yield of 82%.

$^1$H NMR (500 MHz, $CDCl_3$) δ 7.74 (d, J=2.1 Hz, 1H), 7.63-7.52 (m, 6H), 7.44 (dd, J=10.6, 4.8 Hz, 2H), 7.38 (dd, J=8.5, 2.2 Hz, 1H), 7.37-7.32 (m, 1H), 7.14 (d, J=8.5 Hz, 1H), 7.02 (s, 2H), 5.26 (s, 2H), 3.53 (s, 3H). $^{13}$C NMR (126 MHz, $CDCl_3$) δ 153.20, 140.64, 140.42, 136.15, 132.89, 131.05, 128.83, 127.96, 127.39, 127.37, 126.93, 126.89, 126.74, 126.73, 116.14, 113.28, 95.14, 56.43.

8.2 Preparation of (E)-5-(2-([1,1'-biphenyl]-4-yl) vinyl)-2-hydroxybenzoic acid (DC10)

Oxalic acid (3 eq, 63 mg, 759 μmol), $Pd(OAc)_2$ (5%, 3 mg, 13 μmol), Xantphos (5%, 7 mg, 13 μmol), 16 (100 mg, 314 μmol), $H_2O$ (10 eq., 45 mg, 45 μL, 2.53 mmol) and DMF (3 mL) were transferred to a reactor tube, that was sealed and stirred at 100° C. whereupon TEA (3 eq., 77 mg, 106 μL, 759 μmol) was added. $Ac_2O$ (3 eq., 77 mg, 74 μL, 759 μmol) was subsequently added over a period of 15 min by means of a syringe pump. During the addition, CO was produced due to degradation of oxalic acid. The reaction mixture was stirred at 100° C. for 3 h. The reaction mixture was transferred to a separation funnel (250 mL) that was charged with DCM (50 mL) and water (50 mL). The water phase was adjusted to pH 12 and extracted with DCM (3×50 mL). The water phase was then adjusted to pH 1 and extracted using DCM (3×50 mL). The organic phases were combined, dried over anhydrous $Na_2SO_4$, filtered, and concentrated under reduced pressure to obtain the desired product DC10 (37 mg, 117 μmol) as a white solid in a yield of 46%.

$^1$H NMR (500 MHz, DMSO) δ 8.01 (d, J=2.2 Hz, 1H), 7.84 (dd, J=8.7, 2.3 Hz, 1H), 7.73-7.66 (m, 6H), 7.51-7.43 (m, 2H), 7.39-7.34 (m, 1H), 7.31 (d, J=16.5 Hz, 1H), 7.19 (d, J=16.5 Hz, 1H), 7.00 (d, J=8.6 Hz, 1H). $^{13}$C NMR (126 MHz, DMSO) δ 171.72, 160.69, 139.64, 138.88, 13638, 133.08, 128.92, 128.51, 128,50, 127.43, 127.40, 126.86, 126.84, 126.40, 126.31 117.65, 113.20. HR-MS (ESI): $[M-H]^-$: Calcd for $C_{21}H_{15}O_3$ 315.10212, found 315.10201

Example 9

Preparation of 2-hydroxy-5-(naphthalen-2-yl)benzoic acid—DC11

9.1 Preparation of 2-(3-bromo-4-(methoxymethoxy)phenyl)naphthalene (17)

Naphthalen-2-ylboronic acid (1 eq., 250 mg, 1.46 mmol), $K_2CO_3$ (2 eq., 402 mg, 2.92 mmol), and $Pd(PPh_3)_4$ (5%, 84 mg, 73 μmol) were added to a solution of compound 7b (500 mg, 1.46 mmol) in DMF (10 mL). The reaction mixture was flushed with argon and stirred at 100° C. for 2 h. The progress of the reaction was monitored by TLC using hexane:ethyl acetate=9:1 as eluent. The solvent was removed under reduced pressure and the mixture was extracted with DCM (3×50 mL) from water. The organic phases were combined, dried over anhydrous $Na_2SO_4$, filtered, and then concentrated under reduced pressure. The product was purified by means of column chromatography packed with silica gel using hexane:ethyl acetate=99.5:0.5 as eluent. Target compound 17 (361 mg, 1.05 mmol) was obtained as a yellow solid in a yield of 72%.

$^1$H NMR (500 MHz, $CDCl_3$) δ 7.93 (d, J=1.4 Hz, 1H), 7.90 (d, J=2.3 Hz, 1H), 7.87-7.79 (m, 3H), 7.63 (dd, J=8.5, 1.9 Hz, 1H), 7.55 (dd, J=3.8, 1.9 Hz, 1H), 7.50-7.42 (m, 2H), 6.86 (d, J=8.6 Hz, 1H), 5.27 (s, 2H), 3.53 (s, 3H), $^{13}$C NMR (126 MHz, $CDCl_3$) δ 153.86, 136.67, 136.36, 133.68, 132.62, 132.14, 128.61, 128.20, 127.70, 127.34, 126.46, 126.08, 125.46, 125.14, 117.87, 116.38, 84.30, 56.47

9.2 Preparation of 2-hydroxy-5-(naphthalen-2-yl)benzoic acid (DC11)

Oxalic acid (3 eq, 79 mg, 874 μmol), $Pd(OAc)_2$ (5%, 3 mg, 15 μmol), Xantphos (5%, 8 mg, 15 μmol), compound 17 (100 mg, 291 μmol), $H_2O$ (10 eq., 53 mg, 53 μL, 2.91 mmol), and DMF (4 mL) were transferred to a reaction tube that was sealed and left for stirring in a preheated oil bath at 100° C. The septum was penetrated with a syringe needle that was attached to a balloon (for pressure equalization during the in-situ CO production). TEA (3 eq., 95 mg, 131 μL, 874 μmol) was then added. $Ac_2O$ (3 eq., 96 mg, 89 μL, 874 μmol) was then added over a period of 15 min. by means of a syringe pump. During the addition, CO was produced due to degradation of oxalic acid. The reaction mixture was continuously stirred at 100° C. for 3 h. The reaction mixture was transferred to a separation funnel (250 mL) that was charged with DCM (50 mL) and water (50 mL). The water phase was adjusted to pH 12 and extracted with DCM (3×50 mL). The water phase was then adjusted to pH 1 and extracted again with DCM (3×50 mL). The organic phases were combined and dried over anhydrous $Na_2SO_4$, filtered, and concentrated under reduced pressure to afford the target product DC11 (41 mg, 155 μmol) as a white solid in a yield of 49%.

$^1$H NMR (500 MHz, DMSO) δ 8.20 (d, J=2.4 Hz, 1H), 8.18 (d, J=1.4 Hz, 1H), 8.02-7.92 (m, 4H), 7.82 (dd, J=8.6, 1.9 Hz, 1H), 7.56-7.48 (m, 2H), 7.12 (d, J=8.6 Hz, 1H). $^{13}$C NMR (126 MHz, DMSO) δ 171.73, 160.66, 136.31, 134.11, 133.36, 131.98, 131.04, 128.53, 128.22, 128.08, 127.44, 126.40, 125.96, 124.67, 124.47, 117.92 (one of the carbon peaks is not visible). HR-MS (ESI): $[M-H]^-$: Calcd for $C_{17}H_{11}O_3$ 263.07082, found 263.07098

Example 10

Preparation of (E)-2-amino-5-styrylbenzoic acid—DC12

(E)-styrylboronic acid (1 eq., 56 mg, 0.380 mmol), $Pd(PPh_3)_4$ (5%, 22 mg, 19 μmol) and $Na_2CO_3$ (2 eq., 81 mg, 0.760 mmol) in water (2 mL) and EtOH (1 mL) were added to a solution of 2-amino-5-iodobenzoic acid (100 mg, 0.380 mmol) in toluene (3 mL). The reaction mixture was flushed with argon and stirring and heated at 100° C. for 2 h. The progress of the reaction was monitored by TLC with DCM: MeOH=9:1 as eluent. The solvent was then removed under reduced pressure. The obtained crude was purified using chromatography column packed with silica gel using DCM: MeOH=9.5:0.5 as eluent with 0.1% of formic acid present. The target compound DC12 (46 mg, 0.192 mmol was obtained as a yellow solid with a yield of 50%.

$^1$H NMR (400 MHz, $CD_3CN$) δ 7.93 (d, J=2.1 Hz, 1H), 7.58 (dd, J=2.1, 8.7 Hz, 1H), 7.52 (d, J=7.4 Hz, 2H), 7.34 (t, J=7.6 Hz, 2H), 7.23 (d, J=7.3 Hz, 1H),7.11 (d, J=16.4 Hz, 1H), 6.98 (d, J=16.5 Hz, 1H), 6.77 (d, J=8.6 Hz, 1H). $^{13}$C NMR (126 MHz, $CD_3CN$) δ 169.35, 151.84, 138.51, 132.20, 130.86, 129.22, 128.61, 127.52, 126.56, 125.65, 125.22, 117.61, 109.78. HR-MS (ESI): $[M+H]^+$: Calcd for $C_{15}H_{14}NO_2$, 240.10245 found 240.10267; $[M-CO_2—H]^+$: Calcd for $C_{14}H_{12}N$, 194.09697 found 194.09691

Example 11

Preparation of (E)-2-hydroxy-5-(4-(methylsulfonyl)styryl)benzoic acid—DC13

Oxone (3 eq. 120 mg, 0.196 mmol) in water (1 mL) was slowly added to a solution of compound DC08 (15 mg, 52 μmol) in THF (1 mL) and methanol (1 mL). The reaction mixture was stirred for 24 h at 20° C. Acidic water (50 mL) was added to the post reaction mixture and extracted with DCM (3×50 mL). The organic phases were combined, dried over anhydrous $Na_2SO_4$, filtered, and concentrated under reduced pressure. The crude product was purified using a chromatography column packed with silica gel (DCM: methanol=95:5) to afford target DC13 as an off-white solid in a yield of 85% (14 mg, 44 μmol).

$^1$H NMR (500 MHz, DMSO) δ 8.05 (d, J=2.2 Hz, 1H), 7.91-7.80 (m, 5H), 7.48 (d, J=16.5 Hz, 1H), 7.26 (d, J=16.5 Hz, 1H), 7.02 (d, J=8.6 Hz, 1H), 3.22 (s, 3H). $^{13}$C NMR (126 MHz, DMSO) δ 171.62, 161.25, 142.40, 138.82, 133.38, 131.02, 129.20, 127.79, 127.37, 126.76, 124.99, 117.75, 113.38, 43.58. HR-MS (ESI): $[M-H]^-$: Calcd for $C_{16}H_{13}O_5S$ 317.04837, found 317.04806.

Example 12

Preparation of (E)-2-hydroxy-5-(4-(N-phenylsulfamoyl)styryl)benzoic acid DC14

12.1 Preparation of 4-iodo-N-phenylbenzenesulfonamide (18)

4-Iodobenzenesulfonyl chloride (1.62 g, 5.37 mmol) and TEA (1.1 eq., 597 mg, 823 mL, 5.91 mmol) were transferred to a flask that contained anhydrous DCM (20 mL). The reaction was cooled at 0° C. whereupon aniline (1 eq., 500 mg, 5.37 mmol) was added dropwise. The reaction was stirred at 20° C. for 18 h. The mixture was then extracted with DCM (3×250 mL) from a solution of HCl (0.1 M). The organic phases were combined, dried over anhydrous $Na_2SO_4$, filtered, and concentrated under reduced pressure to afford the target product compound 18 (1.76 g, 4.90 mmol) as a yellow oil in a yield of 91%.

$^1$H NMR (500 MHz, $CDCl_3$) δ 7.79 (d, J=8.5 Hz, 2H), 7.45 (d, J=8.5 Hz, 2H), 7.27 (t, J=7.6 Hz, 2H), 7.15 (t, J=7.6 Hz, 1H), 7.06 (d, J=7.6 Hz, 2H), 6.59 (s, 1H). $^{13}$C NMR (126 MHz, $CDCl_3$) δ 138.67, 138.34, 136.02, 129.51, 128.60, 125.84, 121.90, 100.68.

12.2 Preparation of (E)-4-(3-bromo-4-(methoxymethoxy)styryl)-N-phenylbenzenesulfonamide (19)

4-Iodo-N-phenylbenzenesulfonamide 18 (700 mg, 1.95 mmol), $Pd(OAc)_2$ (8%, 35 mg, 156 μmol), $K_2CO_3$ (2 eq., 539 mg, 3.90 mmol), compound 7b (1 eq., 474 mg, 1.95 mmol) and DMF (10 mL) were transferred to a reactor tube that was sealed. The reactor tube was flushed with Argon and sonicated for 5 min. using an ultrasonic bath. The reactor tube was then immersed into the microwave reactor cavity of a microwave oven for 4 h at 100° C. The reaction progress was monitored by means of TLC, using hexane:ethyl acetate=9:1. The solvent was removed under reduced pressure. The mixture was extracted with DCM (3×100 mL) from water using DCM. The combined organic phases were dried over anhydrous $Na_2SO_4$, filtered, and then the solvent was removed under reduced pressure. The crude was purified using column chromatography packed with silica gel and hexane:ethyl acetate=9:1 as eluent to obtain target compound 19 (365 mg, 769 μmol) as a white solid with a yield of 39%.

$^1$H NMR (500 MHz, $CDCl_3$) δ 7.77 (d, J=8.5 Hz, 2H), 7.66 (d, J=2.1 Hz, 1H), 7.62 (s, 1H), 7.42 (d, J=8.5 Hz, 2H), 7.29 (dd, J=2.1, 8.6 Hz, 1H), 7.18-7.23 (m, 2H), 7.12-7.17 (m, 2H), 7.03-7.12 (m, 2H), 6.96 (d, J=16.3 Hz, 1H), 6.84 (d, J=16.3 Hz, 1H), 5.22 (s, 2H), 3.49 (s, 3H). $^{13}$C NMR (126 MHz, $CDCl_3$, 27° C.) δ 153.84, 141.78, 137.37, 136.70, 131.80, 131.40, 130.14, 129.37, 127.79, 127.24, 126.72, 126.27, 125.30, 121.53, 116.02, 113.31, 95.04, 56.46.

12.3 Preparation of (E)-2-hydroxy-5-(4-(N-phenylsulfamoyl)styryl)benzoic acid (DC14)

Oxalic acid (3 eq, 51 mg, 570 μmol), $Pd(OAc)_2$ (5%, 2 mg, 9 μmol), Xantphos (5%, 5 mg, 9 μmol), compound 19 (90 mg, 189 μmol), $H_2O$ (10 eq., 34 mg, 34 μL, 1.90 mmol), and DMF (4 mL) were transferred to a reaction tube that then was sealed. The reaction mixture was heated at 100° C. and stirred and TEA (3 eq., 57 mg, 79 μL, 570 μmol) was added. Then $Ac_2O$ (3 eq., 58 mg, 54 μL, 570 μmol) was added over a period of 15 min. by means of a syringe pump. CO was produced due to degradation of oxalic acid. It is advisable to add a balloon to the sealed vial in order to avoid problem with the increasing pressure. The reaction was stirred at 100° C. for 3 h, and then extracted with DCM (3×50 mL) from HCl (0.1 M). The combined organic phases were dried over anhydrous $Na_2SO_4$, filtered, and the solvent was removed under reduced pressure. The crude was purified through chromatography column packed with silica gel using DCM:methanol=9:1 and 1% formic acid as eluent to afford the title compound DC14 (39 mg, 98 μmol) with a yield of 52%.

$^1$H NMR (500 MHz, DMSO) δ 10.23 (s, 1H), 7.99 (s, 1H), 7.80 (d, J=8.4 Hz, 1H), 7.71 (s, 4H), 7.38 (d, J=16.4 Hz, 1H), 6.96-7.27 (m, 7H). $^{13}$C NMR (126 MHz, DMSO, 27° C.) δ 171.58, 160.78, 141.69, 137.71, 137.48, 134.46, 133.22, 130.85, 129.13, 128.69, 127.13, 126.62, 126.00, 124.89, 124.06, 120.09, 117.74. $[M-H]^-$: Calcd for $C_{21}H_{16}NO_5S$ 394.07492, found 394.07482.

Example 13

Preparation of (E)-4-styryl-2-(1H-tetrazol-5-yl)phenol—DC15

13.1 Preparation of 5-iodo-2-(methoxymethoxy)benzonitrile (20)

2-Hydroxybenzonitrile (2.0 g, 16.79 mmol) in acetonitrile (15 mL) cooled at 0° C. was transferred to a flask (25 mL) that was wrapped in aluminum foil. para-Toluenesulfonic acid monohydrate (1.1 eq., 3.51 g, 18.47 mmol) and N-iodosuccinimide (1.1 eq., 4.16 g, 18.47 mmol) were added to the mixture that was stirred at 20° C. for 18 h. The progress of the reaction was monitored by TLC using hexane:ethyl acetate=8:2 as eluent. The solvent was removed under reduced pressure. The crude was diluted with DCM and a saturated solution of $Na_2S_2O_3$ in water. The aqueous phase was extracted further with DCM (2×250 mL). The organic phases were combined, dried over anhydrous $Na_2SO_4$, filtered, and then concentrated under reduced pressure to obtain 2-hydroxy-5-benzonitrile that was dissolved in anhydrous DCM (20 mL) to proceed with the following reaction. The same flask was cooled at 0° C. and NaH 60% (3 eq., 2.01 g, 50.32 mmol) and chloromethyl methyl ether (1.5 eq., 2.03 g, 1.91 mL, 25.16 mmol) were added. The reaction was heated to 20° C. for 1 h and then quenched using a sat. $NaHCO_3$ (aq.). The mixture was extracted with DCM (3×250 mL). The organic phases were combined over anhydrous $Na_2SO$, filtered, and concentrated under reduced pressure to obtain compound 21 (4.1 g, 14.18 mmol) as a yellow oil in a yield of 84%.

$^1H$ NMR (500 MHz, $CDCl_3$) δ 7.84 (d, J=2.2 Hz, 1H), 7.78 (dd, J=2.2, 8.9 Hz, 1H), 7.03 (d, J=8.9 Hz, 1H), 5.28 (s, 2H), 3.51 (s, 3H). $^{13}C$ NMR (126 MHz, $CDCl_3$) δ 158.89, 143.03, 141.48, 117.02, 114.73, 105.14, 94.91, 82.89, 56.75.

13.2 Preparation of 2-(methoxymethoxy)-5-vinylbenzonitrile (21)

Compound 20 (1.00 g, 3.46 mmol), $Pd(PPh_3)_2$ (8%, 319 mg, 276 μmol), tributyl(vinyl)stannane (1.1 eq., 1.21 g, 3.81 mmol) and DMF (10 mL) were transferred to a reactor tube that then was sealed. The mixture was flushed with Argon, and sonicated for 5 min. Then the reactor tube was immersed into the reactor cavity of a microwave oven and heated at 100° C. for 2 h. The progress of the reaction was monitored by TLC with hexane:ethyl acetate=9:1 as eluent. The solvent was removed under reduced pressure and the mixture was extracted in DCM (3×100 mL) from water. The combined organic phases were dried over anhydrous $Na_2SO_4$, filtered, and the solvent was removed under reduced pressure. The crude was purified using a chromatography column packed with silica gel using hexane:ethyl acetate=95:5 as eluent to obtain target compound 21 (603 mg, 3.19 mmol) as a yellow oil in a yield of 92%.

$^1H$ NMR (500 MHz, $CDCl_3$) δ 7.46 (d, J=2.3 Hz, 1H), 7.43 (dd, J=2.3, 8.8 Hz, 1H), 7.08 (d, J=8.8 Hz, 1H), 6.50 (dd, J=10.9, 17.6 Hz, 1H), 5.56 (d, J=17.5 Hz, 1H), 5.14-5.18 (m, 4H), 3.40 (s, 3H). $^{13}C$ NMR (126 MHz, $CDCl_3$) δ 158.38, 134.25, 131.87, 131.00, 121.91, 116.16, 115.05, 114.50, 103.01, 94.84, 56.53.

13.3 Preparation of (E)-2-(methoxymethoxy)-5-styrylbenzonitrile (22)

Compound 21 (250 mg, 1.32 mmol), 2,3-di(pyridin-2-yl) pyrazine (5%, 16 mg, 66 μmol), $Pd(OAc)_2$ (5%, 15 mg, 66 μmol), phenylboronic acid (1.1 eq., 177 mg, 1.45 mmol), $Cu(OAc)_2$ monohydrate (1.5 eq., 396 mg, 1.98 mmol) and DMF (6 mL) were transferred to a flask. The reaction mixture was stirred at 20° C. in 18 h. The progress of the reaction was monitored by TLC using hexane:ethyl acetate=9:1 as eluent. The mixture was extracted with DCM (3×50 mL) from a solution of EDTA in water (0.2 M). The organic phases were combined, dried over anhydrous $Na_2SO_4$, filtered, and concentrated under reduced pressure. The mixture was purified using a column chromatography packed with silica gel with using hexane:ethyl acetate=99.4:0.6 as eluent. Target compound 22 (288 mg, 1.09 mmol) was obtained as a white solid in a yield of 82%.

$^1H$ NMR (500 MHz, $CDCl_3$) δ 7.71 (d, J=2.2 Hz, 1H), 7.64 (dd, J=2.3, 8.8 Hz, 1H), 7.48-7.51 (m, 2H), 7.32-7.4 (m, 2H), 7.27-7.31 (m, 1H), 7.23 (d, J=8.8 Hz, 1H), 7.01 (d, J=3.5 Hz, 2H), 5,31 (s, 2H), 3.54 (s, 3H). $^{13}C$ NMR (126 MHz, $CDCl_3$) δ 158.23, 136.69, 132.10, 131.79, 131.21, 129.45, 128.82, 128.08, 126.57, 125.86, 116.28, 115.24, 103.30, 94.90, 56.67.

13.4 Preparation of (E)-4-styryl-2-(1H-tetrazol-5-yl) phenol (DC15)

Compound 22 (90 mg, 339 μmol), sodium azide (1.1 eq., 24 mg, 373 μmol), ammonium chloride (10%, 2 mg, 34 μmol) and LiCl (1 eq., 14 mg, 339 μmol) and DMF (3 mL) were transferred to a reactor tube that was sealed and flushed with Ar, whereupon the mixture was heated at reflux for 18 h. The crude was extracted with DCM (3×50 mL) from HCl (0.1 M). The combined organic phases were dried over anhydrous $Na_2SO_4$, filtered, and the solvent was removed under reduced pressure. The crude was purified through chromatography column packed with silica gel using formic acid (0.1%) in DCM as eluent to obtain target compound DC15 (47 mg, 178 μmol) as an off-white solid in a yield of 52%.

$^1H$ NMR (500 MHz, DMSO) δ 8.22 (d, J=2.1 Hz, 1H), 7.71 (dd, J=2.1, 8.7 Hz, 1H), 7.61 (d, J=7.5 Hz, 2H), 7.38 (t, J=7.6 Hz, 2H), 7.24-7.33 (m, 2H), 7.04-7.19 (m, 2H). $^{13}C$ NMR (126 MHz, DMSO) δ 154.95, 137.18, 130.36, 128.93, 128.67, 127.40, 127.34, 127.21, 126.71, 126.28, 116.77, 110.90. $[M-H]^-$: Calcd for $C_{15}H_{11}N_4O_1$ 263.09329, found 263.09343.

Example 14

Preparation of (E)-2-acetamido-5-styrylbenzoic acid—DC16

14.1 Preparation of N-(2-bromo-4-formylphenyl)acetamide (23)

N-(4-formylphenyl)acetamide (2.0 g, 12.26 mmol) in water (20 mL) was transferred to an aluminum foil wrapped flask. N-Bromosuccinimide (1.1 eq., 2.40 g, 13.48 mmol) was then slowly added to the reaction mixture that was stirred at 20° C. for 18 h. The progress of the reaction was monitored by using TLC using hexane:ethyl acetate=8:2 as eluent. The solvent was removed under reduced pressure. The crude was diluted with DCM (100 mL) and a saturated solution of $Na_2S_2O_3$ in water (100 mL). The aqueous phase was extracted further with DCM (2×100 mL). The organic phases were combined, dried over anhydrous $Na_2SO_4$, filtered, and concentrated under reduced pressure to obtain target compound 23 (2.76 g, 11.40 mmol) as a yellow oil and in a yield of 93%.

$^1$H NMR (500 MHz, $CDCl_3$) δ 9.88 (s, 1H), 8.63 (d, J=8.5 Hz, 1H), 8.09 (d, J=1.9 Hz, 1H), 7.82 (dd, J=1.8, 8.5 Hz, 1H), 2.77 (s, 1H), 2.30 (s, 3H). Data consistent with literature.

14.2 Preparation of N-(2-bromo-4-vinylphenyl)acetamide (24)

A suspension of NaH 60% (3 eq., 2.50 g, 30.98 mmol) in anhydrous DCM (20 mL) was slowly added to compound 11 (1.2 eq., 5.01 g, 12.39 mmol) at 0° C., which was stirred for 30 min. Then, compound 23 (2.50 g, 10.33 mmol) was added to the mixture and stirred at 20° C. for 16 h. The reaction mixture was then quenched using sat. $NaHCO_3$ in water. The crude mixture was extracted with DCM (3×250 mL), dried over anhydrous $Na_2SO_4$, filtered, and purified using column chromatography packed with silica gel with hexane:ethyl acetate=9:1 as eluent to obtain the desired compound 24 (2.01 g, 8.37 mmol) as a transparent oil in a yield of 81%.

$^1$H NMR (500 MHz, $CDCl_3$) δ 8.31 (d, J=8.4 Hz, 1H), 7.58 (d, J=1.8 Hz, 1H), 7.35 (dd, J=1.9, 8.5 Hz, 1H), 6.60 (dd, J=10.9, 17.6 Hz, 1H), 5.69 (d, J=17.5 Hz, 1H), 5.25 (d, J=10.9 Hz, 1H), 2.24 (s, 3H).

14.3 Preparation of (E)-N-(2-bromo-4-styrylphenyl) acetamide (25)

Compound 24 (500 mg, 2.08 mmol), 2,3-di(pyridin-2-yl) pyrazine (5%, 24 mg, 104 μmol), $Pd(OAc)_2$ (5%, 23 mg, 104 μmol), phenylboronic acid (1.1 eq., 279 mg, 2.29 mmol), and $Cu(OAc)_2$ monohydrate (1.5 eq., 623 mg, 3.12 mmol) were dissolved in DMF (8 mL). The reaction mixture was stirred at 20° C. for 18 h. The reaction progress was monitored by TLC using hexane:ethyl acetate=9:1 as eluent. The mixture was extracted with DCM (3×50 mL) from a solution of EDTA in water (0.2 M). The organic phases were combined, dried over anhydrous $Na_2SO_4$, filtered, and concentrated under reduced pressure. The mixture was purified column chromatography packed with silica gel using hexane:ethyl acetate=95:5 to obtain target product 25 (241 mg, 0.762 mmol) as a white solid in a yield of 36%.

$^1$H NMR (500 MHz, $CDCl_3$) δ 8.27 (d, J=8.5 Hz, 1H), 7.59-7.63 (m, 1H), 7.55 (s, 1H), 7.41 (d, J=7.4 Hz, 2H), 7.36 (dd, J=1.8, 8.6 Hz, 1H), 7.28 (t, J=7.6 Hz, 2H), 7.15-7.23 (m, 1H), 6.86-6.99 (m, 2H), 2.16 (s, 3H). $^{13}$C NMR (126 MHz, $CDCl_3$, 27° C.) δ 168.10, 136.91, 134.83, 134.71, 131.45, 129.81, 129.26, 128.75, 127.91, 126.56, 126.52, 121.68, 113.42, 22.72

14.4 Preparation of (E)-2-acetamido-5-styrylbenzoic acid (DC16)

Oxalic acid (3 eq., 85 mg, 948 μmol), $Pd(OAc)_2$ (5%, 4 mg, 16 μmol), Xantphos (5%, 9 mg, 16 μmol), compound 25 (100 mg, 316 μmol), $H_2O$ (10 eq., 57 mg, 57 μL, 3.16 mmol) and DMF (5 mL) were transferred to a reaction tube, which was sealed and stirred and heated at 100° C. The septum was penetrated with a syringe needle that was attached to a balloon (for pressure equalization during the in-situ CO production). TEA (3 eq., 96 mg, 132 μL, 948 μmol) was then added. $Ac_2O$ (3 eq., 97 mg, 89 μL, 948 μmol) was added over a period of 15 min. by means of a syringe pump. During the addition CO was formed through degradation of the oxalic acid. The reaction mixture was stirred and heated at 100° C. for 3 h. Then the reaction mixture was extracted with DCM (3×50 mL) from HCl (0.1 M). The combined organic phases were dried over anhydrous $Na_2SO_4$, filtered, and the solvent was removed under reduced pressure. The crude was purified with a chromatography column packet with silica gel using DCM:methanol=9:1 and 1% formic acid as eluent to obtain title compound DC16 (38 mg, 135 μmol) in a yield of 42%.

$^1$H NMR (500 MHz, DMSO) δ 11.26 (s, 1H), 8.49 (d, J=8.7 Hz, 1H), 8.17 (d, J=2.0 Hz, 1H), 7.85 (dd, J=2.0, 8.7 Hz, 1H), 7.62 (d, J=7.4 Hz, 2H), 7.38 (t, J=7.7 Hz, 2H), 7.19-7.32 (m, 4H), 2.15 (s, 3H). $^{13}$C NMR (126 MHz, DMSO) δ 169.33, 168.36, 140.04, 136.98, 131.32, 131.03, 129.26, 128.68, 128.36, 127.96, 127.59, 127.17, 126.44, 120.09, 25.01.

Example 15

Preparation of (E)-5-(2-([1,1'-biphenyl]-3-yl)vinyl)-2-hydroxybenzoic acid—DC18

15.1 Preparation of 3-bromo-4-(methoxymethoxy)-1,1':4',1"-terphenyl (26)

Compound 7b (500 mg, 1.46 mmol) in DMF (10 mL) was added to [1,1'-byphenyl]-4-ylboronic acid (1 eq., 288 mg, 1.46 mmol), $K_2CO_3$ (2 eq., 402 mg, 2.92 mmol), and $Pd(PPh_3)_4$ (5%, 84 mg, 73 μmol). The reaction mixture was flushed with argon and stirred for 2 h at 100° C. The progress of the reaction was monitored by TLC using hexane:ethyl acetate=9:1 as eluent. The solvent was then removed under reduced pressure and the mixture was extracted with DCM (3×50 mL) from water. The organic phases were combined and dried over anhydrous $Na_2SO_4$, filtered, and concentrated under reduced pressure. The crude was purified using column chromatography packed with silica gel using hexane:ethyl acetate=99.5:0.5. Target compound 26 (234 mg, 0.633 mmol) was obtained as a yellow solid in a yield of 43%.

$^1$H NMR (500 MHz, $CDCl_3$) δ 7.83 (d, J=2.2 Hz, 1H), 7.55-7.67 (m, 6H), 7.49 (dd, J=2.3, 8.5 Hz, 1H), 7.44 (t, J=7.6 Hz, 2H), 7.31-7.38 (m, 1H), 7.21 (d, J=8.6 Hz, 1H), 5.27 (s, 2H), 3.54 (s, 3H). $^{13}$C NMR (126 MHz, $CDCl_3$, 27° C.) δ 153.25, 140.59, 140.24, 138.29, 135.99, 131.82, 128.88, 127.61, 127.46, 127.18, 127.07, 126.98, 116.35, 113.36, 95.19, 56.47.

15.2 Preparation of (E)-3-(3-bromo-4-(methoxymethoxy)styryl)-1,1'-biphenyl (27)

Compound 12 (500 mg, 2.06 mmol), 2,3-di(pyridin-2-yl) pyrazine (5%, 24 mg, 102 μmol), $Pd(OAc)_2$ (5%, 23 mg, 102 μmol), [1,1'-biphenyl-3-ylboronic acid (1.1 eq., 448 mg, 2.26 mmol), and $Cu(OAc)_2$ monohydrate (1.5 eq., 615 mg, 3.09 mmol) were transferred to a reaction flask (25 mL) and dissolved in DMF (8 mL). The reaction mixture was stirred at 20° C. for 18 h. The progress of the reaction was monitored by TLC with hexane:ethyl acetate=9:1 as eluent. The mixture was extracted with DCM (3×50 mL) from a solution EDTA in water (0.2 M). The organic phases were combined, dried over anhydrous $Na_2SO_4$, filtered, and concentrated under reduced pressure. The mixture was purified using column chromatography packed with silica gel with hexane:ethyl acetate=99.5:0.5 as eluent to obtain title compound 27 (698 mg, 1.77 mmol) as a white solid in a yield of 86%.

$^{1}H$ NMR (500 MHz, $CDCl_3$) δ 7.77 (d, J=2.2 Hz, 1H), 7.71 (t, J=1.6 Hz, 1H), 7.61-7.67 (m, 2H), 7.37-7.51 (m, 7H), 7.16 (d, J=8.5 Hz, 1H), 7.07 (s, 2H), 5.28 (s, 2H), 3.55 (s, 3H). $^{13}C$ NMR (126 MHz, $CDCl_3$, 27° C.) δ 153.27, 141.79, 141.09, 137.59, 132.83, 131.11, 129.16, 128.82, 128.38, 127.46, 127.22, 127.07, 126.79, 126.61, 125.39, 125.34, 116.14, 113.29, 95.15, 56.44

15.3 Preparation of (E)-5-(2-([1,1'-biphenyl]-3-yl) vinyl)-2-hydroxybenzoic acid (DC18)

Oxalic acid (3 eq., 102 mg, 1.14 mmol), $Pd(OAc)_2$ (5%, 4 mg, 19 μmol), Xantphos (5%, 11 mg, 19 μmol), compound 27 (150 mg, 379 μmol), $H_2O$ (10 eq., 68 mg, 68 μL, 3.79 mmol), and DMF (7 mL) were transferred to a reactor tube that was sealed. The septum was penetrated with a syringe needle that was attached to a balloon (for pressure equalization during the in-situ CO production). The mixture was stirred and heated at 100° C. whereupon TEA (3 eq., 115 mg, 158 μL, 1.14 mmol) was added. $Ac_2O$ (3 eq., 116 mg, 107 μL, 1.14 mol) was then added over a period of 15 min. by means of a syringe pump. During the addition, CO was formed through the degradation of the oxalic acid. The reaction mixture was then stirred at 100° C. for 3 h. The reaction mixture was extracted with DCM (3×50 mL) from HCl (0.1 M). The combined organic phases were dried over anhydrous $Na_2SO_4$, filtered, and the solvent was removed under reduced pressure. The crude was purified using a chromatography column packed with silica gel with 1% formic acid in DCM as eluent to obtain target compound DC18 (52 mg, 164 μmol) in a yield of 43%.

$^{1}H$ NMR (500 MHz, DMSO) δ 7.96 (d, J=2.2 Hz, 1H), 7.84 (s, 1H), 7.78 (dd, J=2.3, 8.7 Hz, 1H), 7.66 (dd, J=1.0, 8.1 Hz, 2H), 7.52 (d, J=7.7 Hz, 1H), 7.48 (d, J=7.9 Hz, 1H), 7.37-7.44 (m, 3H), 7.3-7.35 (m, 2H), 7.16 (d, J=16.5 Hz, 1H), 6.94 (d, J=8.6 Hz, 1H). $^{13}C$ NMR (126 MHz, DMSO, 27° C.) δ 171.77, 160.69, 140.55, 140.06, 137.83, 133.11, 129.24, 128.88, 128.58, 128.53, 127.75, 127.52, 126.75, 126.71, 125.68, 125.38, 124.63, 117.67, 113.14. $[M-H]_-$: Calcd for $C_{21}H_{15}O_3$ 315.10212, found 315.10192.

Example 16

Preparation of (E)-5-(2-([1,1'-biphenyl]-2-yl)vinyl)-2-hydroxybenzoic acid—DC19

16.1 Preparation of (E)-2-(3-bromo-4-(methoxymethoxy)styryl)-1,1'-biphenyl (28)

Compound 12 (500 mg, 2.06 mmol), 2,3-di(pyridin-2-yl) pyrazine (5%, 24 mg, 102 μmol), $Pd(OAc)_2$ (5%, 23 mg, 102 μmol), [1,1'-biphenyl-2-ylboronic acid (1.1 eq., 448 mg, 2.26 mmol), and $Cu(OAc)_2$ monohydrate (1.5 eq., 615 mg, 3.09 mmol) were transferred to a flask and dissolved with DMF (8 mL) that was stirred at 20° C. for 18 h. The progress of the reaction was monitored by TLC using hexane:ethyl acetate=9:1 as eluent. The mixture was extracted with DCM (3×50 mL) from a solution EDTA in water (0.2 M). The organic phases were combined and dried over anhydrous $Na_2SO_4$, filtered, and concentrated under reduced pressure. The mixture was purified using column chromatography packed with silica gel using hexane:ethyl acetate=99.5:0.5 as eluent to obtain title compound 28 (654 mg, 1.65 mmol) as a white solid in a yield of 80%.

$^{1}H$ NMR (500 MHz, $CDCl_3$) δ 7.62 (d, J=7.4 Hz, 1H), 7.46 (d, J=2.1 Hz, 1H) 7.23-7.39 (m, 9H), 7.13-7.17 (m, 1H), 6.99 (d, J=8.5 Hz, 1H), 6.79-6.94 (m, 2H), 5.14 (s, 2H), 3.42 (s, 3H). $^{13}C$ NMR (126 MHz, $CDCl_3$) δ 153.04, 141.15, 140.82, 135.22, 133.22, 131.32, 130.37, 129.89, 128.20, 127.69, 127.64, 127.61, 127.58, 127.22, 126.49, 12584, 116.15, 113.16, 95.11, 56.41.

16.2 Preparation of (E)-5-(2-([1,1'-biphenyl]-2-yl) vinyl)-2-hydroxybenzoic acid (DC19)

Oxalic acid (3 eq., 102 mg, 1.14 mmol), $Pd(OAc)_2$ (5%, 4 mg, 19 μmol), Xantphos (5%, 11 mg, 19 μmol), compound 28 (150 mg, 379 μmol), $H_2O$ (10 eq., 68 mg, 68 μL, 3.79 mmol) and DMF (7 mL) were transferred to a reactor tube that was sealed. The septum was penetrated with a syringe needle that was attached to a balloon (for pressure equalization during the in-situ CO production). The reaction mixture was stirred at 100° C., whereupon TEA (3 eq., 115 mg, 158 μL, 1.14 nmol) was then added. $Ac_2O$ (3 eq., 116 mg, 107 μL, 1.14 mol) was added over a period of 15 min. using a syringe pump resulting in production of CO through degradation of the oxalic acid. The reaction was stirred at 100° C. for 3 h. The mixture was extracted with DCM (3×50 mL) from HCl (0.1 M). The combined organic phases were dried over anhydrous $Na_2SO_4$, filtered, and the solvent was then removed under reduced pressure. The crude was purified by column chromatography packed with silica gel using formic acid (1%) in DCM as eluent to obtain the title compound DC19 (56 mg, 177 μmol) in a yield of 46%.

$^{1}H$ NMR (500 MHz, DMSO) δ 7.89 (d, J=7.5 Hz, 1H), 7.86 (d, J=2.2 Hz, 1H), 7.51-7.6 (m, 3H), 7.44-7.5 (m, 2H), 7.39-7.44 (m, 3H), 7.36 (dd, J=1.4, 7.6 Hz, 1H), 7.24 (d, J=16.4 Hz, 1H), 6.92-7.01 (m, 2H). $^{13}C$ NMR (126 MHz, DMSO) δ 171.61, 160.68, 140.36, 134.64, 132.76, 131.58, 130.10, 129.52, 128.34, 128.31, 127.71, 127.52, 127.26, 125.67, 125.12, 117.74, 113.20. $[M-H]^-$: Calcd for $C_{21}H_{15}O_3$ 315.10212, found 315.10188.

Example 17

Preparation of 6-hydroxy-2,4-dimethyl-3-(naphthalen-2-yl)benzoic acid—DC20

17.1 Preparation of 2-bromo-4-iodo-3,5-dimethylphenol (29)

p-Toluenesulfonic acid monohydrate (1.1 eq., 844 mg, 4.43 mmol), N-Bromosuccinimide (1.1 eq., 789 mg, 4.43 mmol), 4-Iodo-3,5-dimethylphenol (1 g, 4.03 mmol), and acetonitrile (15 mL) were transferred to a flask (25 mL) that was cooled at 0° C. The reaction flask was wrapped in aluminum foil and the mixture was stirred at 20° C. for 18 h. The reaction mixture was monitored by means of TLC using as hexane:ethyl acetate as eluent. The solvent was then removed under reduced pressure, whereupon the isolated crude was diluted with DCM (50 mL) and a sat. $Na_2S_2O_3$ (aq.) (50 mL). The aqueous phase was extracted with DCM (2×50 mL). The organic phases were combined, dried over anhydrous $Na_2SO_4$, filtered, and concentrated under reduced pressure to obtain the title compound 29 (1.23 g, 3.76 mmol) as a yellow solid and in a yield of 93%.

$^{1}H$ NMR (500 MHz, $CDCl_3$) δ 6.87 (s, 2H), 5.68 (s, 2H), 2.72 (s, 6H), 2.42 (s, 7H). $^{13}C$ NMR (126 MHz, $CDCl_3$) δ 151.98, 142.36, 140.50, 114.18, 109.05, 96.65, 30.74, 29.86.

17.2 Preparation of 2-bromo-4-iodo-1-(methoxymethoxy)-3,5-dimethylbenzene (30)

NaH 60% (3 eq., 451 mg, 11.29 mmol) and DCM (15 mL) were transferred to a flask under inert and anhydrous conditions. The suspension was cooled at 0° C. whereupon compound 29 (1.23 g, 3.76 mmol) was slowly added and the mixture was stirred for 10 min. Chloromethyl methyl ether (1.5 eq., 454 mg, 0.428 mL, 5.64 mmol) was then added dropwise. The reaction mixture was then heated at 20° C. and stirred for 1 h. The reaction mixture was then quenched with a sat. $NaHCO_3$ (aq.) and extracted with DCM (3×50 mL). The organic phases were combined, dried over anhydrous $Na_2SO_4$, filtered, and concentrated under reduced pressure to obtain compound 30 (1.27 g, 3.42 mmol) as a yellow oil in a yield of 91%.

$^1$H NMR (500 MHz, $CDCl_3$) δ 6.95 (s, 1H), 5.22 (s, 2H), 3.51 (s, 3H), 2.75 (s, 3H), 2.45 (s, 3H). $^{13}$C NMR (126 MHz, $CDCl_3$) δ 153.42, 141.78, 141.67, 114.31, 111.50, 99.27, 95.08, 56.43, 30.85, 30.32.

17.3 Preparation of 2-(3-bromo-4-(methoxymethoxy)-2,6-dimethylphenyl)naphthalene (31)

Compound 30 (1.27 g, 3.42 mmol) in DMF (15 mL) was added to naphthalen-2-ylboronic add (1 eq., 589 mg, 3.42 mmol), $K_2CO_3$ (2 eq., 946 mg, 6.85 mmol) and $Pd(PPh_3)_4$ (5%, 198 mg, 171 μmol). The reaction mixture was then flushed with argon and stirred at 100° C. for 2 h. The reaction mixture was monitored by means of TLC using hexane:ethyl acetate=9:1 as eluent. The solvent was then removed under reduced pressure and the mixture was extracted with DCM (3×100 mL) from water. The organic phases were combined, dried over anhydrous $Na_2SO_4$, filtered, and concentrated under reduced pressure. The crude was purified using column chromatography packed with silica gel and hexane:ethyl acetate=99.5:0.5 as eluent. Target compound 31 (585 mg, 1.58 mmol) was obtained as a yellow solid in a yield of 46%.

$^1$H NMR (500 MHz, $CDCl_3$) δ 7.87-7.80 (m, 1H), 7.59 (s, 1H), 7.56-7.49 (m, 2H), 7.24 (dd, J=8.3, 1.5 Hz, 1H), 7.00-6.97 (m, 1H), 5.31 (s, 2H), 3.60 (s, 3H), 2.17 (s, 3H), 2.01 (s, 3H). $^{13}$C NMR (126 MHz, $CDCl_3$) δ 152.64, 138.46, 137.62, 136.91, 136.30, 133.53, 132.37, 128.22, 128.09, 127.94, 127.82, 127.78, 126.20, 125.95, 114.75, 113.35, 95.19, 56.47, 21.85, 21.27.

17.4 Preparation of 6-hydroxy-2,4-dimethyl-3-(naphthalen-2-yl)benzoic acid (DC20)

Oxalic acid (3 eq., 291 mg, 3.23 mmol), $Pd(OAc)_2$ (5%, 12 mg, 54 μmol), Xantphos (5%, 32 mg, 54 μmol), 31 (400 mg, 1.08 mmol), $H_2O$ (10 eq., 194 mg, 194 μL, 10.8 mmol) and DMF (7 mL) were transferred to a reaction tube that was sealed. The septum was penetrated with a syringe needle that was attached to a balloon (for pressure equalization during the in-situ CO production). The reaction mixture was then stirred and heated at 100° C. whereupon TEA (3 eq., 327 mg, 450 μL, 3.23 mmol) was added. $Ac_2O$ (3 eq., 329 mg, 305 μL, 2.23 mol) was added over a period of 15 min. by means of syringe pump. The reaction was stirring at 100° C. for 3 h. The mixture was extracted with DCM (3×50 mL) from HCl 0.1 M. The combined organic phases were dried over $Na_2SO_4$, filtered, and the solvent was removed under reduced pressure. The crude was purified using a chromatography column packed with silica gel with 1% formic acid in DCM as eluent to obtain target compound DC20 (65 mg, 222 μmol) in a yield of 20%.

$^1$H NMR (600 MHz, DMSO) δ 7.99-7.90 (m, 3H), 7.65 (d, J=0.9 Hz, 1H), 7.56-7.52 (m, 2H), 7.25 (dd, J=8.3, 1.7 Hz, 1H), 6.69 (s, 1H), 1.98 (s, 3H), 1.91 (s, 3H). $^{13}$C NMR (151 MHz, DMSO) δ 171.09, 155.69 138.80, 138.37, 134.71, 133.64, 133.10, 132.26, 128.66, 128.55, 128.44, 128.26, 128.04, 126.61, 126.35, 119.71, 115.14, 21.50, 19.01. $[M-H]^-$: Calcd for $C_{19}H_{15}O_3$ 291.10212, found 291.10244. $[M-CO_2-h]^-$: Calcd for $C_{18}H_{15}O$ 247.11229 found 247.11603

17.5 Preparation of (E)-2-(3-bromo-4-(methoxymethoxy)styryl)-9,9-dimethyl-9H-fluorene (32)

Compound 12 (500 mg, 2.06 mmol), 2,3-di(pyridin-2-yl) pyrazine (5%, 24 mg, 102 μmol), $Pd(OAc)_2$ (5%, 23 mg, 102 μmol), (9,9-dimethyl-9H-fluorene-2-yl)boronic acid (1.1 eq., 538 mg, 2.26 mmol), and $Cu(OAc)_2$ monohydrate (1.5 eq., 615 mg, 3.09 mmol) were transferred to a reactor tube and dissolved in DMF (8 mL) and then stirred for 18 h at 20° C. The progress of the reaction was monitored by means of TLC using hexane:ethyl acetate=9:1 as eluent. The mixture was extracted with DCM (3×50 mL) from a solution of EDTA in water (0.2 M). The organic phases were combined, dried over anhydrous $Na_2SO_4$, filtered, and concentrated under reduced pressure. The mixture was purified using a chromatography column packed with silica gel with hexane: ethyl acetate=99.5:0.5 as eluent to obtain title compound 32 (803 mg, 1.84 mmol) as a white solid in a yield of 89%.

$^1$H NMR (500 MHz, $CDCl_3$) δ 7.64 (d, J=2.1 Hz, 1H), 7.55-7.6 (m, 1H), 7.54 (d, J=7.8 Hz, 1H), 7.43-7.46 (m, 1H), 7.31 (s, 2H), 7.24 (dd, J=2.1, 8.5 Hz, 1H), 7.17-7.21 (m, 2H), 7.00 (d, J=8.5 Hz, 1H), 6.93 (d, J=7.7 Hz, 2H), 5.11 (s, 2H), 3.39 (s, 3H), 1.39 (s, 6H). $^{13}$C NMR (126 MHz, $CDCl_3$, 27° C.) δ 154.22, 153.97, 153.18, 139,14, 138.95, 136.37, 133.15, 131.07, 128.96, 127.39, 127.15, 126.71, 126.14, 125.97, 122.68, 120.47, 120.35, 120.12, 116.20, 113.36, 95.18, 56.45, 46.85, 27.29.

Example 18

Preparation of (E)-5-(2-(9,9-dimethyl-9H-fluoren-2-yl)vinyl)-2-hydroxybenzoic acid DC21

Oxalic acid (3 eq., 102 mg, 1.14 mmol), $Pd(OAc)_2$ (5%, 4 mg, 19 μmol), Xantphos (5%, 11 mg, 19 μmol), compound 32 (165 mg, 379 μmol), $H_2O$ (10 eq., 68 mg, 68 μL, 3.79 mmol), and DMF (7 mL) were transferred to a reactor tube that was sealed and stirred at 100° C. The septum was penetrated with a syringe needle that was attached to a balloon (for pressure equalization during the in-situ CO production). TEA (3 eq., 115 mg, 158 μL, 1.14 mmol) was then added. $Ac_2O$ (3 eq., 116 mg, 107 μL, 1.14 mol) was added over a period of 15 min. by means of a syringe pump. The reaction mixture was then stirred at 100° C. for 3 h. The reaction mixture was extracted with DCM (3×50 mL) from HCl 0.1 M. The organic phases were combined and dried over anhydrous $Na_2SO_4$, filtered, and the solvent was removed under reduced pressure. The crude was purified by means of a chromatography column packed with silica gel with 1% formic acid in DCM as eluent to obtain title compound DC21 (61 mg, 171 μmol) with a yield of 45%.

$^1$H NMR (500 MHz, DMSO) δ 8.05 (d, J=2.2 Hz, 1H), 7.82-7.86 (m, 2H), 7.77-7.82 (m, 2H), 7.51-7.56 (m, 2H), 7.28-7.39 (m, 3H), 7.22 (d, J=16.4 Hz, 1H), 7.02 (d, J=8.6 Hz, 1H), 1.47 (s, 6H). $^{13}$C NMR (126 MHz, DMSO) δ 171.82, 160.63, 153.80, 153.52, 138.34, 137.95, 136.52, 132.96, 128.71, 128.45, 127.24, 127.21, 127.04, 126.84, 125.94, 122.73, 120.29, 120.27, 120.04, 117.69, 113.17, 26.86. $[M-H]^-$: Calcd for $C_{24}H_{19}O_3$ 355.13342, found 355.13312.

Example 19

Preparation of 4-hydroxy-[1,1':4',1"-terphenyl]-3-carboxylic acid—DC17

Oxalic acid (3 eq., 92 mg, 1.03 mmol), $Pd(OAc)_2$ (5%, 4 mg, 17 μmol), Xantphos (5%, 10 mg, 17 μmol), compound 26 (127 mg, 344 μmol), $H_2O$ (10 eq., 62 mg, 62 μL, 3.44 mmol) and DMF (7 mL) were transferred to a reactor tube, which was sealed and stirred in a preheated oil bath at 100° C. The septum was penetrated with a syringe needle that was attached to a balloon (for pressure equalization during the in-situ CO production) and TEA (3 eq., 104 mg, 144 μL, 1.03 mmol) was then added, followed by addition of $Ac_2O$ (3 eq., 105 mg, 97 μL, 1.03 mol) over a period of over 15 min. using a syringe pump. During the addition of $Ac_2O$, CO was formed through degradation of the oxalic acid. The reaction mixture was stirred at 100° C. for 3 h. The mixture was extracted with DCM (3×50 mL) from HCl (0.1 M). The combined organic phases were dried over anhydrous $Na_2SO_4$, filtered, and the solvent was removed under reduced pressure. The crude was purified using chromatography column packed with silica gel using 1% formic acid in DCM as eluent to obtain title compound DC17 (49 mg, 169 μmol) in a yield of 49%.

$^1H$ NMR (500 MHz, DMSO) δ 7.95 (d, J=1.3 Hz, 1H), 7.86 (dd, J=2.3, 8.6 Hz, 1H), 7.71-7.77 (m, 6H), 7.61-7.66 (m, 1H), 7.46-7.53 (m, 2H), 7.05 (d, J=8.5 Hz, 1H). $^{13}C$ NMR (126 MHz, DMSO, 27° C.) δ 167.29, 162.30, 139.60, 138.58, 138.24, 132.85, 130.73, 129.24, 128.97, 128.55, 127.45, 127.20, 126.57, 126.49, 117.71. $[M-H]^-$: Calcd for $C_{19}H_{14}O_3$ 289.08647, found 289.08732.

Example 20

In Vitro Testing in Cancer Cell Lines

The cancer cell lines A172, A375, U87 and MCF7 were purchased from American Type Culture Collection (ATCC; Manassas, Va., USA). Cells were cultured in Dulbecco's Modified Eagle's Medium (DMEM) supplemented with 10% fetal bovine serum, 2% v/v L-glutamine, 3.2% v/v non-essential amino acids, antibiotics 2% v/v (penicillin-streptomycin), and 0.02% v/v Plasmocin at 37° C. and 5% $CO_2$.

xCT expression of cancer cell lines was evaluated by western blotting from protein samples of cell lysates as described in Sleire et al., Oncogene 34: 5951-5959, 2015. Protein concentrations were determined by BCA assay (Thermo Fisher Scientific, USA) followed by SDS PAGE and immunoblotting using rabbit anti-xCT (Thermo Fisher Scientific) and rabbit anti-GAPDH (Abcam, Cambridge, UK) as a loading control. The compounds were dissolved in dimethylsulfoxide (DMSO) (Sigma Aldrich, Germany) and stock concentrations of 100 mM were stored at −20° C. in aliquots. Final concentrations were made in growth medium before adding to the cell monolayers.

The compounds were evaluated based on the measurement of intracellular Glutathione (GSH) which was performed by the GSH-Glo assay (Promega, Madison, WI, USA, cat #V6912) according to the manufacturer's recommended procedures. 5000 cells per well were seeded in a flat bottomed 96-well plate. After attachment to the well surface, cells were exposed to 250 μM and 500 μM of each compound for 48 h. After that, GSH-Glo reagent was added followed by short incubation and addition of luciferin detection reagent. Bioluminescence was measured using a luminometer (Victor 3 1420 multi-label counter, Perkins Elmer, Waltham, MA, USA). $IC_{50}$ doses for the compounds SAS, DC10 and DC14 were determined in A172 glioma cells, using the GraphPad Prism v6 software (GraphPad Software, Inc. CA, USA). All measurements were normalized to the untreated control and were performed three times. Results are presented in Table 1:

TABLE 1

Intracellular GSH levels measured in different cell lines

| | | | | A172 | | A375 | | MCF7 | | U87 | |
|---|---|---|---|---|---|---|---|---|---|---|---|
| Molecular structure | # | MW | log P | 250 μM | 500 μM | 250 μM | 500 μM | 250 μM | 500 μM | 250 μM | 500 μM |
| 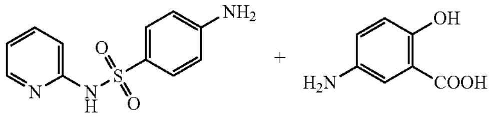 [SMILES: Nc1ccc(S(=O)(=O)Nc2ccccn2)cc1 ; Nc1ccc(O)c(C(=O)O)c1] | MIX | 249.29<br>154.14 | 1.02<br>0.40 | 103.0 | 92.4 | 104.9 | 114.9 | 108.9 | 111.4 | 128.1 | 129.3 |
| 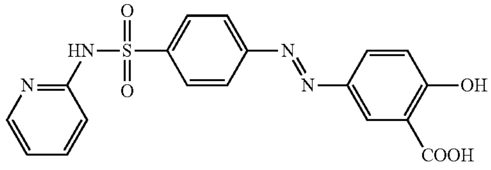 | SAS | 398.39 | 3.42 | 15.0 | 2.1 | 13.5 | 5.3 | 26.2 | 7.6 | 14.0 | 8.0 |
| 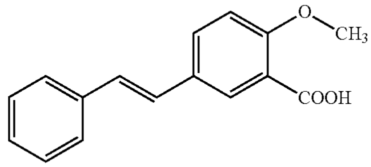 [SMILES: COc1ccc(/C=C/c2ccccc2)cc1C(=O)O] | DC01 | 254.29 | 3.66 | 84.6 | 76.2 | 60.5 | 43.1 | 93.8 | 66.5 | 76.6 | 79.6 |

TABLE 1-continued
Intracellular GSH levels measured in different cell lines
| Molecular structure | # | MW | log P | A172 250 µM | A172 500 µM | A375 250 µM | A375 500 µM | MCF7 250 µM | MCF7 500 µM | U87 250 µM | U87 500 µM |
|---|---|---|---|---|---|---|---|---|---|---|---|
| 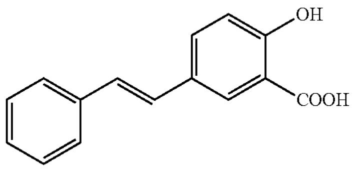 [SMILES: O=C(O)c1cc(/C=C/c2ccccc2)ccc1O] | DC02 | 240.26 | 3.39 | 90.9 | 41.0 | 50.4 | 32.0 | 47.4 | 15.9 | 82.2 | 66.9 |
| 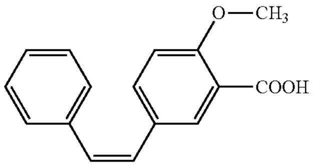 [SMILES: COc1ccc(/C=C\c2ccccc2)cc1C(=O)O] | DC03 | 254.29 | 3.66 | 77.5 | 68.2 | 68.6 | 47.6 | 94.9 | 49.4 | 87.9 | 88.4 |
| 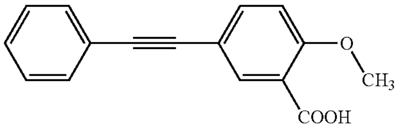 [SMILES: COc1ccc(C#Cc2ccccc2)cc1C(=O)O] | DC04 | 252.27 | 3.41 | 86.9 | 77.6 | 63.4 | 42.4 | 91.4 | 68.0 | 80.6 | 88.6 |
| 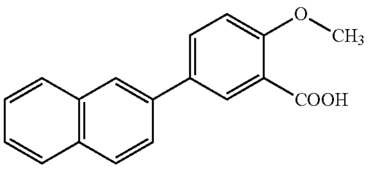 [SMILES: COc1ccc(-c2ccc3ccccc3c2)cc1C(=O)O] | DC05 | 278.31 | 4.14 | 75.6 | 57.7 | 47.6 | 37.9 | 82.4 | 39.0 | 42.9 | 39.5 |
| 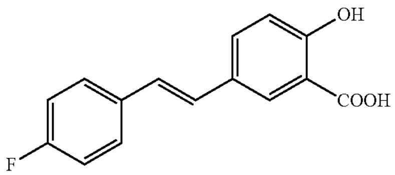 [SMILES: O=C(O)c1cc(/C=C/c2ccc(F)cc2)ccc1O] | DC07 | 258.25 | 3.55 | 81.6 | 16.8 | 23.8 | 7.8 | 22.1 | 6.9 | 50.4 | 11.7 |
| 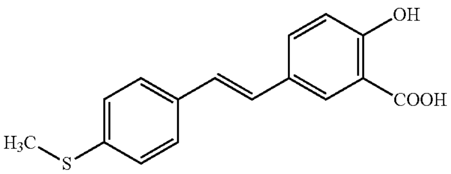 [SMILES: CSc1ccc(/C=C/c2ccc(O)c(C(=O)O)c2)cc1] | DC08 | 286.35 | 3.83 | 28.8 | 9.3 | 25.9 | 3.7 | 21.1 | 6.6 | 51.1 | 8.4 |
| 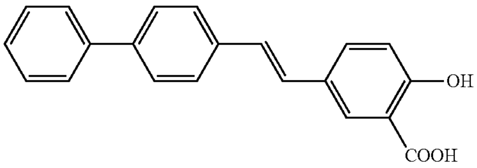 [SMILES: O=C(O)c1cc(/C=C/c2ccc(-c3ccccc3)cc2)ccc1O] | DC10 | 316.36 | 5.07 | 10.4 | 2.3 | 27.6 | 3.1 | 28.0 | 10.9 | 76.1 | 7.3 |
| 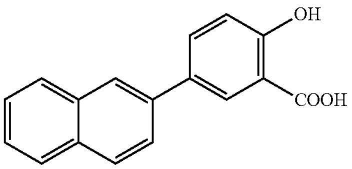 [SMILES: O=C(O)c1cc(-c2ccc3ccccc3c2)ccc1O] | DC11 | 264.28 | 3.87 | 28.4 | 10.2 | 36.1 | 11.8 | 23.7 | 8.8 | 62.6 | 22.7 |

TABLE 1-continued
Intracellular GSH levels measured in different cell lines
| Molecular structure | # | MW | log P | A172 | | A375 | | MCF7 | | U87 | |
|---|---|---|---|---|---|---|---|---|---|---|---|
| | | | | 250 μM | 500 μM | 250 μM | 500 μM | 250 μM | 500 μM | 250 μM | 500 μM |
| 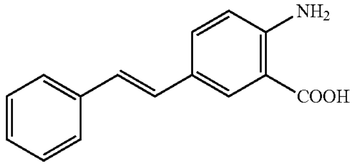 [SMILES: Nc1ccc(/C=C/c2ccccc2)cc1C(=O)O] | DC12 | 239.27 | 2.98 | 107.4 | 101.2 | 116.1 | 95.6 | 115.7 | 96.5 | 103.5 | 117.1 |
| 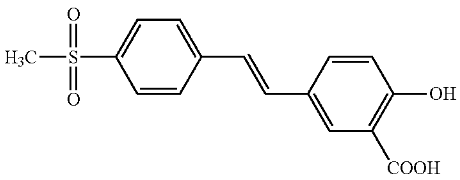 [SMILES: CS(=O)(=O)c1ccc(/C=C/c2ccc(O)c(C(=O)O)c2)cc1] | DC13 | 318.34 | 2.10 | 94.1 | 81.6 | 74.3 | 59.7 | 88.3 | 76.6 | 105.3 | 103.4 |
| 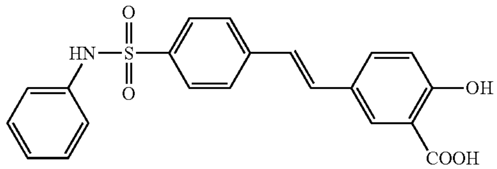 [SMILES: O=C(O)c1cc(/C=C/c2ccc(S(=O)(=O)Nc3ccccc3)cc2)ccc1O] | DC14 | 395.43 | 3.80 | 23.1 | 2.4 | 4.5 | 2.0 | 25.9 | 1.8 | 18.0 | 1.9 |
| 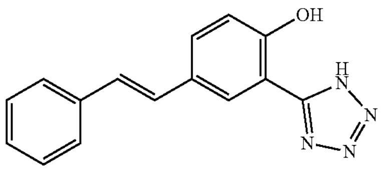 [SMILES: Oc1ccc(/C=C/c2ccccc2)cc1-c1nnn[nH]1] | DC15 | 264.29 | 3.73 | 55.1 | 9.7 | 53.3 | 46.4 | 75.8 | 32.6 | 104.1 | 50.4 |
| 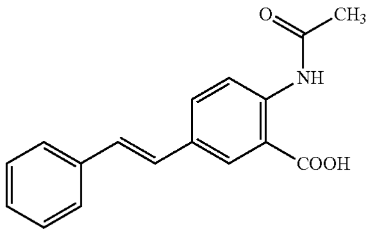 [SMILES: CC(=O)Nc1ccc(/C=C/c2ccccc2)cc1C(=O)O] | DC16 | 281.31 | 2.69 | 67.3 | 51.7 | 34.5 | 26.4 | 92.4 | 83.7 | 73.5 | 63.2 |
| 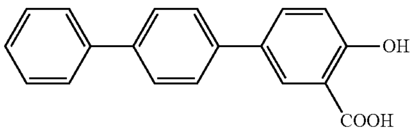 [SMILES: O=C(O)c1cc(-c2ccc(-c3ccccc3)cc2)ccc1O] | DC17 | 290.32 | 4.55 | 98.4 | 28.7 | 56.6 | 4.6 | 51.7 | 17.0 | 66.2 | 20.2 |
| 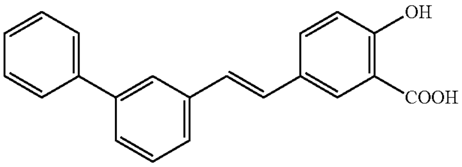 [SMILES: O=C(O)c1cc(/C=C/c2cccc(-c3ccccc3)c2)ccc1O] | DC18 | 316.36 | 5.07 | 73.96 | 3.7 | 53.7 | 3.4 | 54.6 | 4.8 | 66.5 | 4.6 |

TABLE 1-continued

Intracellular GSH levels measured in different cell lines

| Molecular structure | # | MW | log P | A172 250 µM | A172 500 µM | A375 250 µM | A375 500 µM | MCF7 250 µM | MCF7 500 µM | U87 250 µM | U87 500 µM |
|---|---|---|---|---|---|---|---|---|---|---|---|
| 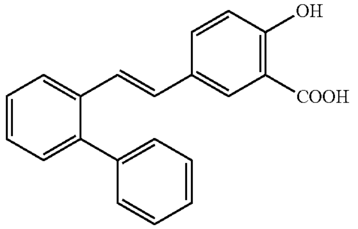 [SMILES: O=C(O)c1cc(/C=C/c2ccccc2-c2ccccc2)ccc1O] | DC19 | 316.36 | 5.07 | 58.7 | 3.3 | 47.8 | 3.7 | 51.0 | 4.3 | 64.6 | 5.0 |
| 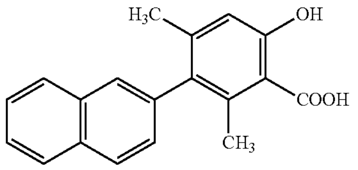 [SMILES: Cc1cc(O)c(C(=O)O)c(C)c1-c1ccc2ccccc2c1] | DC20 | 293.33 | 4.90 | 82.1 | 11.9 | 63.1 | 4.6 | 40.5 | 9.7 | 61.1 | 6.1 |
| 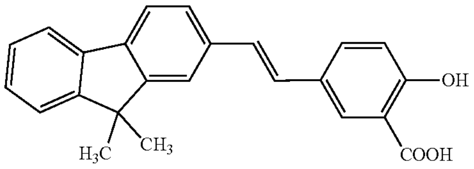 [SMILES: CC1(C)c2ccccc2-c2ccc(/C=C/c3ccc(O)c(C(=O)O)c3)cc21] | DC21 | 356.42 | 5.93 | 4.9 | 2.8 | 4.2 | 3.3 | 5.7 | 4.2 | 5.0 | 3.8 |

MW and log P were calculated using "chemical properties routines" in ChemDraw Professional v 16.0.1.4(61)

Example 21

In Vivo Testing

Experiments were approved by the Norwegian Animal Research Authority (Oslo, Norway) in accordance with the Guide for the Care and Use of Laboratory Animals (Institute for Laboratory Animal Research, National Research Council. Washington, D.C.: National Academy Press, 1996). NOD/Scid mice were kept at the animal facility at Department of Biomedicine at the University of Bergen. The animals were provided a standard pellet diet and tap water ad libitum. They were kept in a pathogen free environment at a constant temperature and humidity, and standard 12/12 h light and dark cycle.

A. Assessment of Toxicity Associated with DC10:

Method:

In order to assess toxicity associated with DC10 it was administered to 6 NOD/Scid mice and compared against a control group of 5 NOD/Scid mice that did not receive the compound. DC10 was dissolved in distilled water and administered as a slurry by oral gavage. 16 mg was administered in a volume of 0.2 ml to each animal. 3 of the animals were observed for 24 hours and 3 animals were observed for 48 hours before sacrifice in $CO_2$-anaesthesia. Blood was sampled through heart puncture with a 3 ml syringe and 0.75 to 1 ml blood was collected. 250 µl was transferred to EDTA tubes that were tilted 15 times to avoid coagulation. The remaining volumes were transferred to 1.5 ml cryotubes and left to coagulate for 3 minutes before centrifugation at 2200 RCF for 10 minutes. This was followed by transfer of the supernatant to new cryotubes that were kept at −20° C., then thawed immediately prior to analysis at the clinical laboratory at Haukeland University Hospital. Blood collected on EDTA tubes underwent hematological analyses, whereas serum underwent biochemical analyses. Organs were also harvested, fixed on 4% formalin embedded in paraffin, sectioned and stained with hematoxylin and esosin.

Results:

The results are provided in FIG. 1A. Hematological analysis revealed normal hemoglobin, thrombocytes and leukocytes. Furthermore, biochemical blood analysis showed no significant elevation in S-Kreatinin (Kidney function), or shift in γ-GT, S-ASAT, S-ALAT, Amylase and S-Glukose (Liver and pancreatic function). Clinical inspection did not reveal any signs, symptoms or deficits. Brain, lungs, heart, intestines, liver, kidneys and spleen which were harvested appeared normal upon macroscopic inspection. The organs did not show evidence of inflammation or other signs of tissue injury when examined histopathologically.

B. Validation of DC10 as a Radiosensitizer In Vivo:

Method:

In this study 20 NOD/Scid mice were grafted with A375 melanoma cells. The A375 cell line was maintained in incubators at 37° C. and 5% $CO_2$ prior to use in the animal experiment. A375 was cultured in DMEM (Sigma-Aldrich, St-Louis, MO, USA) with the supplement of 10% fetal bovine serum (FBS), 3.2% non-essential amino acids, 100 units/mL Penicillin/Streptomycin, 400 mol/L L-glutamine (all Lonza, Cologne, Germany). Cells were passaged in vitro in medium sized 75 $cm^2$ culture flasks. Before the animal experiments, 5 ml of trypsin was added to the culture flasks containing monolayers of A375 cells to detach the cells. Trypsin was inactivated by adding 5 ml of cell culture medium and the cell suspension was spun down at 900 rpm for 5 min. The supernatant was removed and the cell precipitate containing A375 cells were re-suspended in phosphate buffered saline.

For induction of subcutaneous tumours, $5 \times 10^5$ A375 cells were injected in the right flank of 20 NOD/SCID mice, and the animals were randomly assigned to 4 groups with 6 animals in each group. After ten days, animals with comparable tumour size were randomly assigned to four groups: 1) Control (n=6), 2) DC10 (n=6), 3) Radiation (RT) (n=6), and 4) DC10+Radiation (DC10+RT) (n=6). Tumours were measured with calipers and tumour volumes were estimated using the formula ($V = \frac{1}{2}$ (Length×Width$^2$)). Tumour diameter size was measured with a caliper at day 11, 14, 17, 19 and 20. When tumour engraftment was confirmed, 8 mg DC10 was administered on day 14 followed by radiation at day 15, administering 4 Gy with a linear accelerator, at the Department of Oncology at Haukeland University Hospital. During radiation, animals were anesthetized with injection anesthesia administered intraperitoneally (mixture of 56.25 mg/kg ketamine+0375 mg/kg dexmedetomedine in a stock solution to inject 0.1 ml/10 g mouse). The radiation dose was delivered to the region covering the tumour in the flank. When the largest tumours reached a diameter of 20 mm, the experiment was terminated. Tumour growth data for the treatment groups and different time points were analysed with repeated measures for 2-way Anova analysis.

Results:

The results are provided in FIG. 1B. It was found that tumours in the group receiving the combination therapy with DC10 (DC10+RT) were significantly smaller than the tumours in the other groups.

The invention claimed is:

1. A method of treating cancer, said method comprising the step of administering to a patient in need thereof a pharmaceutically effective amount of a compound of general formula (I), a stereoisomer, or a pharmaceutically acceptable salt thereof, in combination with radiotherapy:

(I)

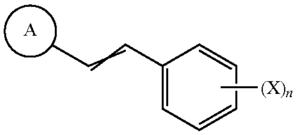

wherein:

ring A is optionally substituted biphenyl;

each X is independently selected from:

—$C_{1-6}$ alkyl,

—O—$C_{1-6}$ alkyl,

—S—$C_{1-6}$ alkyl,

—OH,

—SH,

—$CO_2R^1$ where $R^1$ is H or $C_{1-6}$ alkyl,

—$SO_2$—$C_{1-6}$ alkyl,

—$SO_2$—$NR^2R^3$ where $R^2$ is H and $R^3$ is optionally substituted phenyl,

—$NR^4R^5$ wherein $R^4$ and $R^5$ are independently selected from H, $C_{1-6}$ alkyl, and —CO—$C_{1-6}$ alkyl, halogen, and optionally substituted tetrazolyl;

n is an integer from 0 to 5; and

 denotes an E or Z double bond.

2. The method of claim 1, wherein ring A is unsubstituted biphenyl.

3. A method of treating cancer, said method comprising the step of administering to a patient in need thereof a pharmaceutically effective amount of a compound, a stereoisomer, or a pharmaceutically acceptable salt thereof, in combination with radiotherapy, wherein said compound is selected from the following and their stereoisomers, and pharmaceutically acceptable salts:

| Compound No. | Compound name and CAS No. (where appropriate) | Structure |
|---|---|---|
| DC01 | (E)-2-methoxy-5-styrylbenzoic acid | 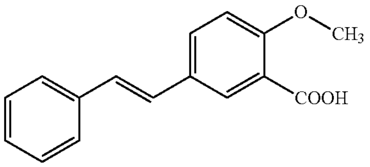 [SMILES: COc1ccc(/C=C/c2ccccc2)cc1C(=O)O] |
| DC02 | (E)-2-hydroxy-5-styrylbenzoic acid CAS 1072937-49-5 | 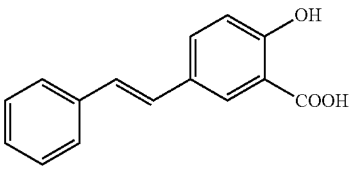 [SMILES: O=C(O)c1cc(/C=C/c2ccccc2)ccc1O] |
| DC03 | (Z)-2-methoxy-5-styrylbenzoic acid | 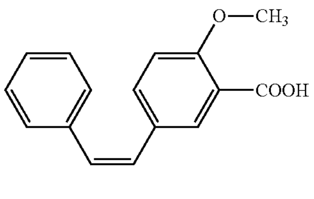 [SMILES: COc1ccc(/C=C\c2ccccc2)cc1C(=O)O] |

-continued

| Compound No. | Compound name and CAS No. (where appropriate) | Structure |
|---|---|---|
| DC07 | (E)-5-(4-fluorostyryl)-2-hydroxybenzoic acid | 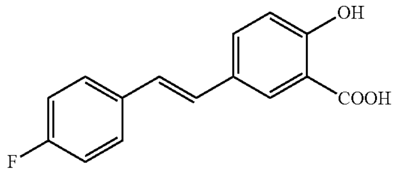 [SMILES: O=C(O)c1cc(/C=C/c2ccc(F)cc2)ccc1O] |
| DC08 | (E)-2-hydroxy-5-(4-(methylthio)styryl)benzoic acid | 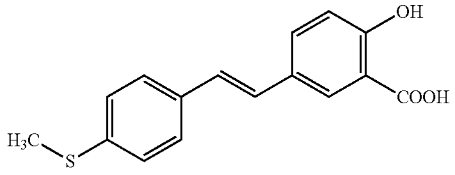 [SMILES: CSc1ccc(/C=C/c2ccc(O)c(C(=O)O)c2)cc1] |
| DC10 | (E)-5-(2-([1,1'-biphenyl]-4-yl)vinyl)-2-hydroxybenzoic acid | 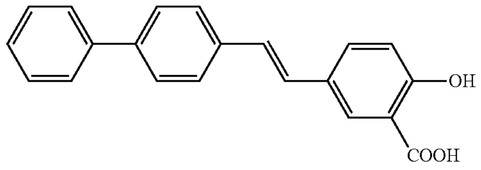 [SMILES: O=C(O)c1cc(/C=C/c2ccc(-c3ccccc3)cc2)ccc1O] |
| DC12 | (E)-2-ammino-5-styrylbenzoic acid | 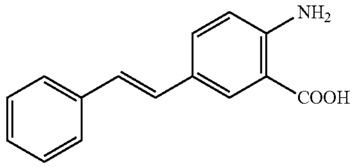 [SMILES: Nc1ccc(/C=C/c2ccccc2)cc1C(=O)O] |
| DC13 | (E)-2-hydroxy-5-(4-(methylsulfonyl)styryl)benzoic acid | 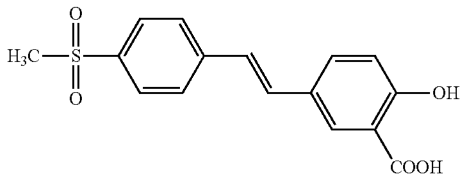 [SMILES: CS(=O)(=O)c1ccc(/C=C/c2ccc(O)c(C(=O)O)c2)cc1] |
| DC15 | (E)-4-styryl-2-(1H-tetrazol-5-yl)phenol | 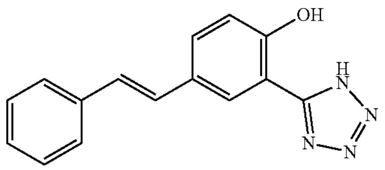 [SMILES: Oc1ccc(/C=C/c2ccccc2)cc1-c1nnn[nH]1] |
| DC16 | (E)-2-acetamido-5-styrylbenzoic acid<br>CAS No. 380365-20-8 | 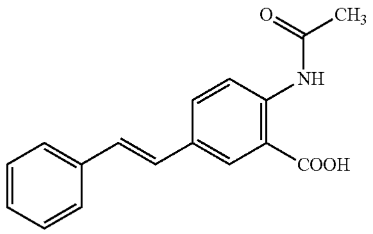 [SMILES: CC(=O)Nc1ccc(/C=C/c2ccccc2)cc1C(=O)O] |
| DC18 | (E)-5-(2-([1,1'-biphenyl]-3-yl)vinyl)-2-hydroxybenzoic acid | 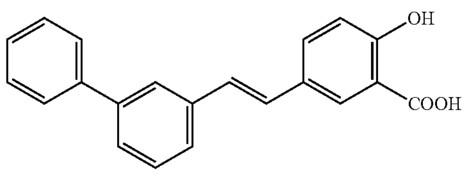 [SMILES: O=C(O)c1cc(/C=C/c2cccc(-c3ccccc3)c2)ccc1O] |

-continued

| Compound No. | Compound name and CAS No. (where appropriate) | Structure |
|---|---|---|
| DC19 | (E)-5-(2-([1,1'-biphenyl]-2-yl)vinyl)-2-hydroxybenzoic acid | 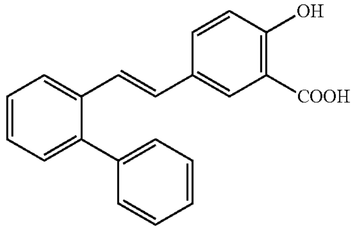 [SMILES: O=C(O)c1cc(/C=C/c2ccccc2-c2ccccc2)ccc1O] |
| DC21 | (E)-5-(2-(9,9-dimethyl-9H-fluoren-2-yl)vinyl)-2-hydroxybenzoic acid | 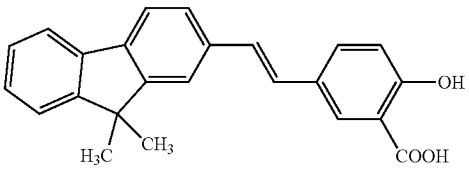 [SMILES: CC1(C)c2ccccc2-c2ccc(/C=C/c3ccc(O)c(C(=O)O)c3)cc21] |

4. The method of claim 1, wherein said cancer is a radioresistant cancer.

5. A method of treating cancer, said method comprising the step of administering to a patient in need thereof a pharmaceutically effective amount of a compound of general formula (I), a stereoisomer, or a pharmaceutically acceptable salt thereof, in combination with radiotherapy:

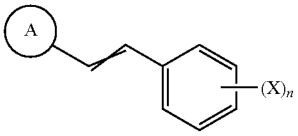

(I)

wherein:

ring A is a fluorenyl group substituted by 1 or 2—$CH_3$ groups;

each X is independently selected from:

—$C_{1-6}$ alkyl,

—O—$C_{1-6}$ alkyl,

—S—$C_{1-6}$ alkyl,

—OH,

—SH,

—$CO_2R^1$ where $R^1$ is H or $C_{1-6}$ alkyl,

—$SO_2$—$C_{1-6}$ alkyl,

—$SO_2$—$NR^2R^3$ where $R^2$ is H and $R^3$ is optionally substituted phenyl,

—$NR^4R^5$ wherein $R^4$ and $R^5$ are independently selected from H, $C_{1-6}$ alkyl, and —CO—$C_{1-6}$ alkyl, halogen, and optionally substituted tetrazolyl;

n is an integer from 0 to 5; and

 denotes an E or Z double bond.

6. The method of claim 5, wherein ring A is 9,9-dimethyl-9H-fluorenyl.

7. The method of claim 4, wherein said cancer is selected from the following: malignant gliomas, medulloblastoma, neuroblastoma, Kaposi's sarcoma, head and neck squamous cell carcinoma, tongue cancer, esophageal squamous cell carcinoma, thyroid cancer, melanoma, breast cancer, prostate cancer, laryngeal squamous cell carcinoma, lung cancer, mesothelioma, gastric cancer, hepatocellular carcinoma, pancreatic cancer, cholangiocarcinoma, colon cancer, renal cancer, urothelial cancer, testis cancer, endometrial cancer, ovarian cancer, cervical cancer, and metastases from any of these cancers, as well as myeloma, lymphoma and leukemia.

8. The method of claim 7, wherein said cancer is glioblastoma multiforme, lung cancer or breast cancer.

9. The method of claim 7, wherein said cancer is glioblastoma multiforme.

10. The method of claim 3, wherein said cancer is a radioresistant cancer.

11. The method of claim 10, wherein said cancer is selected from the following:

malignant gliomas, medulloblastoma, neuroblastoma, Kaposi's sarcoma, head and neck squamous cell carcinoma, tongue cancer, esophageal squamous cell carcinoma, thyroid cancer, melanoma, breast cancer, prostate cancer, laryngeal squamous cell carcinoma, lung cancer, mesothelioma, gastric cancer, hepatocellular carcinoma, pancreatic cancer, cholangiocarcinoma, colon cancer, renal cancer, urothelial cancer, testis cancer, endometrial cancer, ovarian cancer, cervical cancer, and metastases from any of these cancers, as well as myeloma, lymphoma and leukemia.

12. The method of claim 11, wherein said cancer is glioblastoma multiforme, lung cancer or breast cancer.

13. The method of claim 11, wherein said cancer is glioblastoma multiforme.

14. The method of claim 5, wherein said cancer is a radioresistant cancer.

15. The method of claim 14, wherein said cancer is selected from the following:

malignant gliomas, medulloblastoma, neuroblastoma, Kaposi's sarcoma, head and neck squamous cell carcinoma, tongue cancer, esophageal squamous cell carcinoma, thyroid cancer, melanoma, breast cancer, prostate cancer, laryngeal squamous cell carcinoma, lung cancer, mesothelioma, gastric cancer, hepatocellular carcinoma, pancreatic cancer, cholangiocarcinoma, colon cancer, renal cancer, urothelial cancer, testis cancer, endometrial cancer, ovarian cancer, cervical cancer, and metastases from any of these cancers, as well as myeloma, lymphoma and leukemia.

16. The method of claim 15, wherein said cancer is glioblastoma multiforme, lung cancer or breast cancer.

17. The method of claim 15, wherein said cancer is glioblastoma multiforme.

* * * * *